United States Patent
Yanase et al.

(10) Patent No.: US 8,383,377 B2
(45) Date of Patent: Feb. 26, 2013

(54) BACTERIUM CAPABLE OF FERMENTING GLUCOSE, MANNOSE AND XYLOSE SIMULTANEOUSLY, AND METHOD FOR PRODUCTION OF BIOETHANOL USING THE BACTERIUM

(75) Inventors: Hideshi Yanase, Tottori (JP); Kenji Okamoto, Tottori (JP)

(73) Assignee: National University Corporation Tottori University, Tottori-Shi (JP)

( * ) Notice: Subject to any disclaimer, the term of this patent is extended or adjusted under 35 U.S.C. 154(b) by 273 days.

(21) Appl. No.: 12/681,520

(22) PCT Filed: Oct. 3, 2008

(86) PCT No.: PCT/JP2008/068073
§ 371 (c)(1),
(2), (4) Date: Jul. 26, 2010

(87) PCT Pub. No.: WO2009/044868
PCT Pub. Date: Apr. 9, 2009

(65) Prior Publication Data
US 2010/0311140 A1    Dec. 9, 2010

(30) Foreign Application Priority Data

Oct. 5, 2007  (JP) ................................. 2007-261860

(51) Int. Cl.
*C12P 7/06* (2006.01)
*C12P 7/10* (2006.01)
*C12N 1/20* (2006.01)
*C12N 1/00* (2006.01)
*C12N 15/00* (2006.01)

(52) U.S. Cl. ..................... 435/161; 435/165; 435/252.3; 435/243; 435/320.1

(58) Field of Classification Search .................. 435/161, 435/165, 252.3, 243, 320.1
See application file for complete search history.

(56) References Cited

U.S. PATENT DOCUMENTS 5,843,760 A    12/1998 Zhang et al.
7,223,575 B2 *  5/2007 Zhang et al. .................. 435/161

FOREIGN PATENT DOCUMENTS

WO    WO 02/38740 A1    5/2002
WO    WO 2004/037973 A2    5/2004

OTHER PUBLICATIONS

Gunasekaran et al., The SACB and SACC genes encoding levansucrase and sucrase from a gene cluster in *Zymomonas mobilis*. Biotechnol. Lett., 1995, vol. 17 (6): 635-642.*
Kannan et al., Improved ethanol production from sucrose by a mutant of *Zymomonas mobilis* lacking sucrase in immobilized cell fermentation. Enz. Microbial Technol., 1998, vol. 22: 179-184.*
Dien et at "Bacteria engineered for fuel ethanol production: current status", Appl Microbiol Biotechnol, 2003, vol. 63, No. 3, p. 258-266.
Kawakami et al. "Ethanol production from hemicellulosic materials by genetically engineered *Zumomonas mobilis*", Abstracts of the Annual Meeting of the Society for Biotechnology, Japan, 2005, vol. 2005, p. 179.
Weisser et al., "Expression of the *Escherichia coli* pmi Gene, Encoding Phosphomannose-Isomerase in *Zymomonas mobilis*, Leads to Utilization of Mannose as a Novel Growth Substrate, Which Can Be Used as a Selective Marker", Appl and Environ Microbiol, 1996, vol. 62, No. 11, p. 4155-4161.
International Preliminary Report on Patentability issued on May 4, 2010 in International Application No. PCT/JP2008/068073 (PCT/IB/373).
Examiner's Report dated May 15, 2012 issued in corresponding Canadian Patent Application No. 2,700,826.
Extended European Search Report, dated Sep. 1, 2010, for European Application No. 08834910.5.
Yanase et al., "Ethanol production from cellulosic materials by genetically engineered *Zymomonas mobilis*," Biotechnology Letters, vol. 27, pp. 259-263, 2005.

* cited by examiner

*Primary Examiner* — Ganapathirama Raghu
(74) *Attorney, Agent, or Firm* — Birch, Stewart, Kolasch & Birch, LLP

(57) ABSTRACT

The object is to develop a bacterium capable of fermenting glucose, mannose and xylose simultaneously, which can ferment a saccharified solution of a cellulose-type or lignocellulose-type biomass resource to produce ethanol, and to construct an energy-saving high-efficiency bioethanol conversion process. Thus, disclosed is *Zymomonas mobilis* bacterium which is prepared by integrating a gene encoding a phosphomannose isomerase derived from *Escharichia coli* into a levansucrase gene located on the chromosome by the double cross-over by means of a homologous recombsination method, and then introducing recombinant DNA prepared by binding a DNA fragment containing genes encoding a xylose isomerase, a xylulokinase, a transaldolase and a transketolase, respectively, all derived from *Escherichia coli* to a vector. Also disclosed is a method for producing ethanol by continuously fermenting a saccharified solution of a cellulose-type biomass resource in a system on which the *Zymomonas mobilis* bacterium is immobilized.

6 Claims, 14 Drawing Sheets

BACTERIUM CAPABLE OF FERMENTING GLUCOSE, MANNOSE AND XYLOSE SIMULTANEOUSLY, AND METHOD FOR PRODUCTION OF BIOETHANOL USING THE BACTERIUM

TECHNICAL FIELD

The present invention relates to a fermentative bacterial strain capable of fermenting glucose, mannose and xylose simultaneously, and a process for producing bioethanol from a cellulose-type or lignocellulose-type biomass using the bacterial strain.

BACKGROUND ART

In Japan, the output of unused biomass resources, that is, cellulose-type industrial (general) waste materials, such as forest thinnings, construction waste materials, rice straw and rice husk, as well as old paper and waste paper, reaches up to 50 million tons per year. Use of these biomasses as an energy source is considered to be "carbon-neutral" because they do not upset the global $CO_2$ balance, and the biomasses are highly expected as an energy source that contributes to the greenhouse gas reduction. Under such circumstances, it has been suggested and studied to produce ethanol as a biofuel from unused cellulose-type or lignocellulose-type biomass resources and to use the produced bioethanol as a raw material for the syntheses of oxygen-containing compounds for addition to gasoline or chemical products, or as regional heat source and electric power source.

However, there are no fermentative bacteria available in nature, which produce ethanol by directly degrading and fermenting cellulose-type or lignocellulose-type biomass resources. Therefore, it is expected to create a fermentative bacterium capable of fermenting and converting cellulose partial degradation products (cellooligosaccharides), xylose and mannose present as a mixture in an acid-treated saccharified solution of celluloses and hemicelluloses simultaneously into ethanol by using metabolic engineering technologies and cell surface presentation technologies. It is also expected to construct an innovative energy-saving high-efficiency conversion process, wherein a continuous fermentation apparatus having a bred fermentative bacterial strain as a catalyst element is incorporated.

The present inventors previously succeeded in the creation of a transformed microorganism capable of producing ethanol from a pentose by introducing a foreign gene encoding at least one enzyme selected from a xylose isomerase, a xylulokinase, a transaldolase and a transketolase into a microorganism of the genus *Zymobacter* incapable of assimilating a pentose (Patent Document 1). For the purpose of efficient production of ethanol from a raw material containing mannose, the present inventors also succeeded in the creation of a recombinant microorganism by integrating a foreign gene encoding a phosphomannose isomerase into the chromosome of a bacterium of the genus *Zymomonas* to give stable mannose fermentation capacity to the bacterium (Patent Document 2).
Patent Document 1: JP 2005-261421 A
Patent Document 2: JP 2007-14306 A

DISCLOSURE OF THE INVENTION

Problems to be Solved by the Invention

An object of the present invention is to create a fermentative bacterium capable of fermenting glucose, mannose and xylose, simultaneously, which can produce ethanol by fermenting and converting cellooligosaccharides, xylose and mannose present in a saccharified solution obtained from cellulose-type and lignocellulose-type biomass resources of herbaceous origin and particularly of ligneous origin simultaneously into ethanol. Another object of the present invention is to establish an innovative energy-saving high-efficiency bioethanol conversion process suitable for practical use.

Means for Solving the Problems

Bacteria of the genus *Zymomonas* are known as bacteria for brewing tequila, and these bacteria are 3 to 5 times more excellent in the rate of ethanol fermentation and productivity as compared with traditional brewer's yeast, and are also superior to yeast in the ethanol productivity per unit bacterial cells. However, the bacteria of the genus *Zymomonas* are not capable of fermenting maltose or xylose that is present in a saccharified solution of a cellulose-type or lignocellulose-type biomass resource to produce ethanol.

The present inventors aimed at the excellent ethanol productivity of bacteria of the genus *Zymomonas*, and presumed that a bacterium capable of fermenting glucose, mannose and xylose simultaneously could be created by applying the technologies described in the above Patent Documents 1 and 2 filed by the present inventors to achieve the objects mentioned above. Thus, as a result of an intensive study, the present inventors have completed the present invention.

That is, the present invention provides:

(1) A fermentative bacterium capable of fermenting glucose, mannose and xylose simultaneously, which is *Zymomonas mobilis* comprising a gene encoding a phosphomannose isomerase of *Escherichia coli* origin integrated into a levansucrase gene located on the chromosome by double crossover according to a homologous recombination method, and introduced recombinant DNA which is formed by binding a DNA fragment containing genes encoding a xylose isomerase, a xylulokinase, a transaldolase and a transketolase, respectively, all being *Escherichia coli* origin to a vector;

(2) The fermentative bacterium according to the above (1), which is obtainable by using of a high levansucrase producing strain as a host strain;

(3) The fermentative bacterium according to the above (2), wherein the host strain is *Zymomonas mobilis* ZMcs (FERM BP-11024);

(4) The fermentative bacterium according to the above (3), which is *Zymomonas mobilis* ZM mx42 (FERM BP-11025).

(5) A process for producing ethanol comprising allowing a saccharified solution of cellulose-type and/or lignocellulose-type biomass resources and the fermentative bacterium capable of fermenting glucose, mannose and xylose simultaneously according to claim 1, which has been immobilized on an immobilized carrier, to contact with each other, thereby fermenting the saccharified solution to obtain a fermented solution, and recovering ethanol from the fermented solution;

(6) The process for producing ethanol according to the above (5), wherein the fermentative bacterium is *Zymomonas mobilis* ZM mx42 (FERM BP-11025);

(7) The process for producing ethanol according to the above (5), wherein the biomass resource is a ligneous biomass resource; and (8) The process for producing ethanol according to the above (5), wherein the saccharified solution is continuously fed into a reactor packed with the immobilized fermentative bacterium, thereby allowing the saccharified solution and the fermentative bacterium to contact with each other to obtain a fermented solution, collecting the fermented solution continuously, and recovering ethanol therefrom.

Effect of the Invention

In the highly efficient ethanol production from an acid-treated saccharified solution of ligneous and herbaceous biomass resources, it is of importance to give simultaneous fermentation capacity of glucose, mannose and xylose, which are derived from celluloses and hemicelluloses and are present as a mixture in the saccharified solution, to a bacterium to be used. However, Zymomonas mobilis has no fermentation capacity of mannose or xylose, while it has strong glucose fermentation capacity.

As to mannose fermentation capacity, Zymomonas mobilis insufficiently expresses a mannose kinase and a phosphomannose isomerase, particularly a phosphomannose isomerase, which are indispensable for metabolism of mannose. According to the present invention, it is possible to give mannose fermentation capacity to Zymomonas mobilis by introducing and expressing a phosphomannose isomerase gene (manA) of Escherichia coli origin, and further to give stable mannose fermentation capacity by integrating the gene into the chromosome. Furthermore, although the metabolism of xylose in bacteria generally requires four enzymes, i.e., a xylose isomerase and a xylulokinase as well as a transaldolase and a transketolase which are essential enzymes for the pentose phosphate pathway, Zymomonas mobilis lacks a xylose isomerase and a xylulokinase and cannot therefore utilize xylose. Then, according to the present invention, xylose fermentation capacity can be given to Zymomonas mobilis by introducing a xylose isomerase gene (xylA), a xylulokinase gene (xylB), a transaldolase gene (tal) and a transketolase gene (tktA), all being Escherichia coli origin. Thus, the fermentation capacity of three kinds of saccharides i.e., glucose, xylose and mannose, can be given to Zymomonas mobilis by introducing a manA gene and genes of the enzyme system of xylose metabolism.

The ethanol fermentation can be carried out efficiently by immobilizing the thus-created bacterial strain capable of fermenting glucose, mannose and xylose simultaneously on an immobilization carrier to construct a reactor for the continuous production of bioethanol, and continuously introducing a saccharified solution of a biomass resource into the reactor to allow the saccharified solution and the fermentative bacterial strain to contact with each other.

BEST MODE FOR CARRYING OUT THE INVENTION

Host Strain

The Zymomonas mobilis host to which mannose fermentation capacity is given according to the present invention can be Zymomonas mobilis usually used in ethanol production but, from the viewpoint of increasing the xylose fermentation capacity, preferred is a high levansucrase producing strain described hereinafter which occurs as a result of natural mutation and produces a larger amount of levansucrase than a wild type strain does.

Giving Mannose Fermentation Capacity to Bacterial Strain

The gene that encodes a phosphomannose isomerase (manA) used for giving mannose fermentation capacity can be obtained from Escherichia coli, which is a donor microorganism capable of degrading mannose.

DNA encoding a phosphomannose isomerase of a donor microorganism is separated and purified, and then cleaving the DNA by various methods to obtain a DNA fragment. Further, the DNA fragment is bound to a vector DNA fragment obtainable according to the same manner by means of, for example, a DNA ligase to form recombinant DNA containing a phosphomannose isomerase gene. Techniques such as separation and purification of DNA, preparation of a DNA fragment, and binding by a DNA ligase can be carried out, for example, by using a commercially available DNA extraction kit according to a known method in the pertinent field such as the method described in Molecular Cloning, $3^{rd}$ Edition (J. Sambrook, et al., Cold Spring Harbor Lab. Press, 2001).

Figure 1:
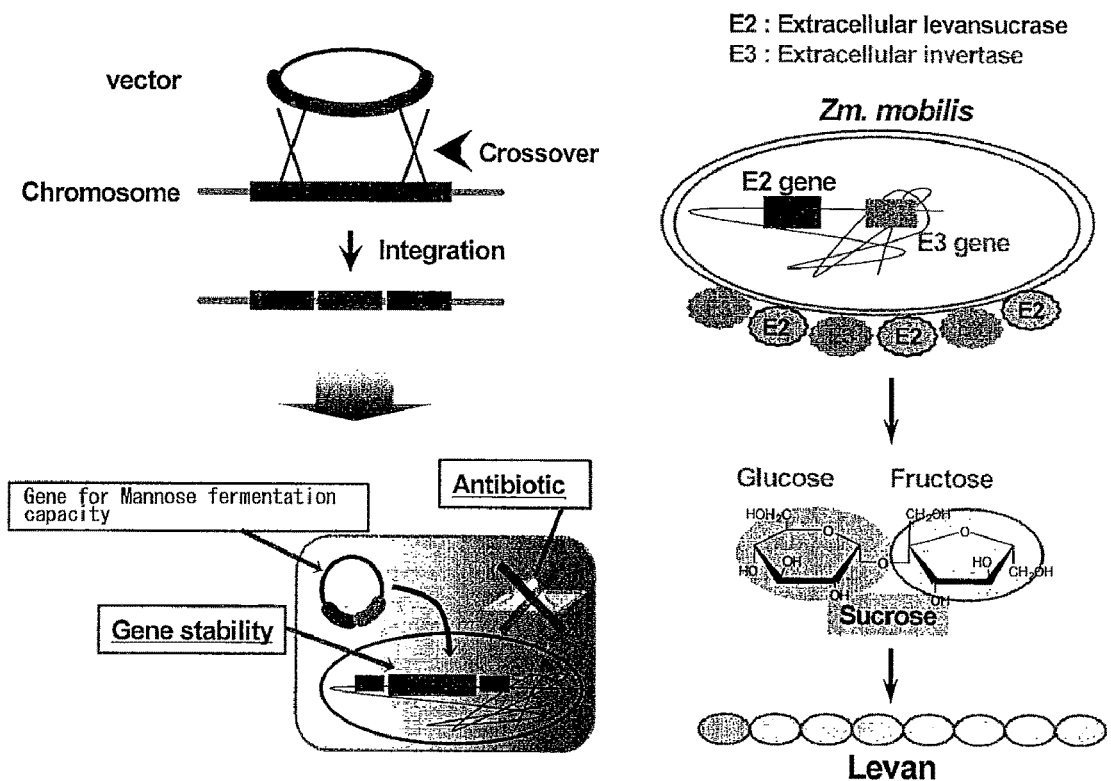
FIG. 1 is a diagram illustrating the procedure for integrating manA into chromosomal DNA.

The integration into the chromosome can be carried out by double crossover according to a known homologous recombination method. That is, a levansucrase gene is cloned as a chromosomal target gene of Zymomonas mobilis, and then a foreign gene encoding a phosphomannose isomerase is inserted into the chromosomal target gene which has been cloned in vitro to prepare DNA wherein parts of the target gene are linked to the upstream and downstream of the foreign gene, respectively, followed by integrating this DNA into the target gene located on the chromosome of *Zymomonas mobilis*. For example, as shown in FIG. 1, a levansucrase gene (hereinafter referred to as E2) is coordinated with an invertase gene (hereinafter referred to as E3) on the chromosomal DNA of *Zymomonas mobilis*. These two enzymes are present on the cell surface of *Zymomonas mobilis*, and releases fructose utilizing sucrose as a substrate, thereby catalyzing a transfer reaction to form levan. The E2 site is targeted, and a phosphomannose isomerase gene is integrated thereinto by double crossover using a homologous recombination method to delete E2. As a result, it is possible to produce ethanol from fructose which forms levan. On the other hand, unlike a vector-introduced strain, the stability of the introduced gene is increased. Thus, an agent such as a marker is not required.

Construction of Recombinant Vector for Giving Xylose Fermentation Capacity

As a microorganism capable of degrading xylose, *Escherichia coli* is used as a DNA donor, and DNAs encoding a xylose isomerase, a xylulokinase, a transaldolase and a transketolase are separated therefrom and purified. Subsequently, the DNAs are cleaved by various methods to prepare DNA fragments encoding the enzymes. These DNA fragments are bound to an appropriate vector DNA fragment, for example, by means of a DNA ligase. Thus, a recombinant DNA containing a xylose isomerase gene, a xylulokinase gene, a transaldolase gene and a transketolase gene is formed.

Separation and purification of a DNA from a donor can be carried out by a per se known method, for example, the method by Saito and Miura (Biochem. Biophys. Acta, Vol. 72, 619-629, 1963) or a modification thereof, or a method using a commercial DNA extraction kit.

The DNAs of the donor microorganism obtained are cleaved by, for example, a restriction enzyme, and DNA fragments of shorter than 1 kbp are eliminated by a sucrose density gradient method. Then, the remaining fragments can be used as donor DNA fragments. The restriction enzyme used at this time is not particularly limited, and it is also possible to cleave DNA by using, for example, ultrasonication, or physical shear force, in addition to the above enzymatic method. At this time, preferably, the termini of the donor DNA fragments are treated with, for example, a Klenow fragment or an enzyme such as a DNA polymerase or a mung bean nuclease because the efficiency of subsequence binding with a vector DNA is increased. Further, a PCR amplification product obtained by using the DNA of the donor microorganism or a fragment thereof as a template can also be used as a donor DNA fragment either directly or after applying the treatments mentioned above.

The vector DNA fragment is not particularly limited but, for example, shuttle vector pZA22 can be suitably used.

The vector DNA fragment obtained can be treated with an alkaline phosphatase prior to the binding reaction with the donor DNA fragments, thereby, enhancing the binding efficiency of the fragment and the donor DNA fragments. Further, in the case of preparing a donor DNA fragment by PCR amplification, the binding efficiency can also be increased by using in advance a primer which gives a restriction site such as EcoRI at both termini of an amplified fragment, while a vector fragment to be used is prepared by cleaving a vector with the same restriction enzyme as that used for cleaving the amplified fragment. The binding reaction of the donor DNA fragments and the vector DNA fragment can be carried out by using a conventional method such as a method using a known DNA ligase. For example, after annealing the donor DNA fragments and the vector DNA fragment, recombinant DNA can be produced ex vivo under the action of an appropriate DNA ligase. If necessary, after annealing, the fragments can be introduced into a host microorganism, and a recombinant DNA can be produced by utilizing the in vivo DNA repair capacity.

Creation of Bacterial Strain Having Simultaneous Fermentation Capacity of Glucose, Mannose and Xylose The recombinant DNA vector containing a xylose isomerase gene, a xylulokinase gene, a transaldolase gene and a transketolase gene is introduced into *Zymomonas mobilis* obtained above to which mannose fermentation capacity has been given.

The method for introducing the recombinant DNA vector is not particularly limited, but introduction of the recombinant DNA is suitably achieved by a method utilizing electrical stimulation, such as electroporation.

The strain into which recombinant DNA vector has been introduced is cultured on a xylose plate medium, and the colonies formed thereon are cultured in a liquid medium containing xylose and mannose as carbon sources. The growth is monitored, and a transformed strain exhibiting high growth in both carbon sources of xylose and mannose is selected to obtain the desired bacterial strain capable of fermenting glucose, mannose and xylose simultaneously.

Construction of Continuous Fermentation Reactor for Saccharified Solution from Biomass Resource The fermentative bacterium of the present invention can be used in the production of ethanol from a saccharified solution of any biomass resource of ligneous type or herbaceous type, but in view of its high ethanol productivity, the bacterium can be suitably used in the production of ethanol from a saccharified solution of a ligneous biomass resource.

For example, a saccharified solution is prepared by hydrolyzing raw material wood through a chemical or physical treatment, and this solution is used as a raw material for fermentation. This saccharified solution of wood contains a mixture of glucose, xylose and mannose derived from celluloses and hemicelluloses which are constituent components of wood.

Bioethanol has been produced hitherto by batch type or continuous type fermentation of a saccharified solution of wood with yeast which is used as a traditional brewer's fungus. In such a production process, xylose or mannose contained in a saccharified solution of wood (approximately 20%) cannot be converted into bioethanol. Then, recovery of bioethanol from a saccharified solution of wood has been limited to only that from the glucose component (approximately 50%). This is a factor in increasing the cost of bioethanol.

In the present invention, bioethanol can be produced at high speed with a high recovery rate by using the fermentative bacterial strain described above by continuously feeding a saccharified solution of wood to a reactor packed with the bacterial strain which has been immobilized on an immobilization carrier to allow the saccharified solution and the fermentative bacterial strain to contact with each other. Then, it is possible to achieve a further recovery of bioethanol of about 20% corresponding to the amount of xylose and mannose, and cost reduction, as compared with a conventional method.

The immobilization onto an immobilization carrier can be carried out according to a per se known method such as an inclusion method, a physical adsorption method, or a covalent bonding method.

A suitable carrier is that having, for example, a hollow shape, a concavo-convex shape, or a porous shape and having a large surface area per unit volume, or that swelling by water absorption. The suitable carrier should have fluidity and sufficient particle size and specific gravity to prevent it from easily flowing out of a reaction system. The carrier can be in the form of, for example, plate, fiber, a special shape such as cylinder, sponge, granules or mass, or cube. Among them, fine granules are preferred because of easy securing of fluidity and sufficient surface area. The usable material includes various organic and inorganic materials which have been conventionally used as those of carriers for microorganisms or enzymes. Examples thereof include inorganic materials such as granular activated carbon, pulverized activated carbon, wood charcoal, zeolite, mica and sand grains; resin materials such as photocurable resins, polyurethane, polyvinyl alcohol, polyethylene, polyacrylamide, polyester, polypropylene, agar, alginic acid, carrageenan, cellulose, dextran, agarose and ion-exchanged resins; porous ceramics such as silica gel; anthracite; diatomaceous earth; and a mixture of resin materials and activated carbon. They can be used alone or in a combination of two or more thereof.

The immobilization carrier is usually used by packing a bioreactor with it. Examples of the bioreactor used for fermentation include reactors of complete mixing tank type, packed bed type, membrane type, fluid bed type, and horizontal type according to the difference in mechanisms and function. Such a bioreactor is suitably used because the bioreactor makes it possible to carry out continuous fermentation without requiring feeding and recovery of a microorganism.

When carrying out the alcohol fermentation as described above, various nutrient sources for the microorganism can be incorporated into the saccharified solution where necessary and, for example, a yeast extract, corn steep liquor, peptone, a meat extract, and a bonito extract can be used as nitrogen sources.

Hereinafter, the present invention will be described in more detail by the following Examples, but the present invention is not intended to be limited thereto.

Example 1

Integration of Phosphomannose Isomerase Gene (manA)

(1) Cloning of Phosphomannose Isomerase Gene (manA) of *Escherichia coli* (*E. coli*) Origin A DNA fragment containing a target gene was amplified by PCR using a combination of the synthetic oligonucleotides shown in Table 1 which were designed based on a known glyceraldehyde-3-phosphate dehydrogenase gene sequence of *Zymomonas mobilis* (*Zm. mobilis*) origin (J. Bacteriol. Vol. 169 (12), 5653-5662, 1987) and a known manA nucleotide sequence of *E. coli* origin (Gene 32 (1-2), 41-48 (1984)).

First, primary PCR was carried out using the chromosomal DNA (Chr. DNA) of a wild strain of *Zm. mobilis* (IFO13756) as a template to amplify the gap promoter. Similarly, manA was amplified using the Chr. DNA of *E. coli* K12 strain as a template. Then, the two PCR products were used to form a hetero-double strand. Secondary PCR was carried out to construct a gap-manA fragment, and this fragment was ligated to the HincII site of vector pUC118. *E. coli* JM109 strain was transformed with the resulting product.

Sequencing of the inserted fragment was carried out and, as a result, the nucleotide sequence of the inserted fragment was confirmed to be consistent with the nucleotide sequence of manA registered in a database. Thus, the product was named pUC118-manA.

Figure 2:
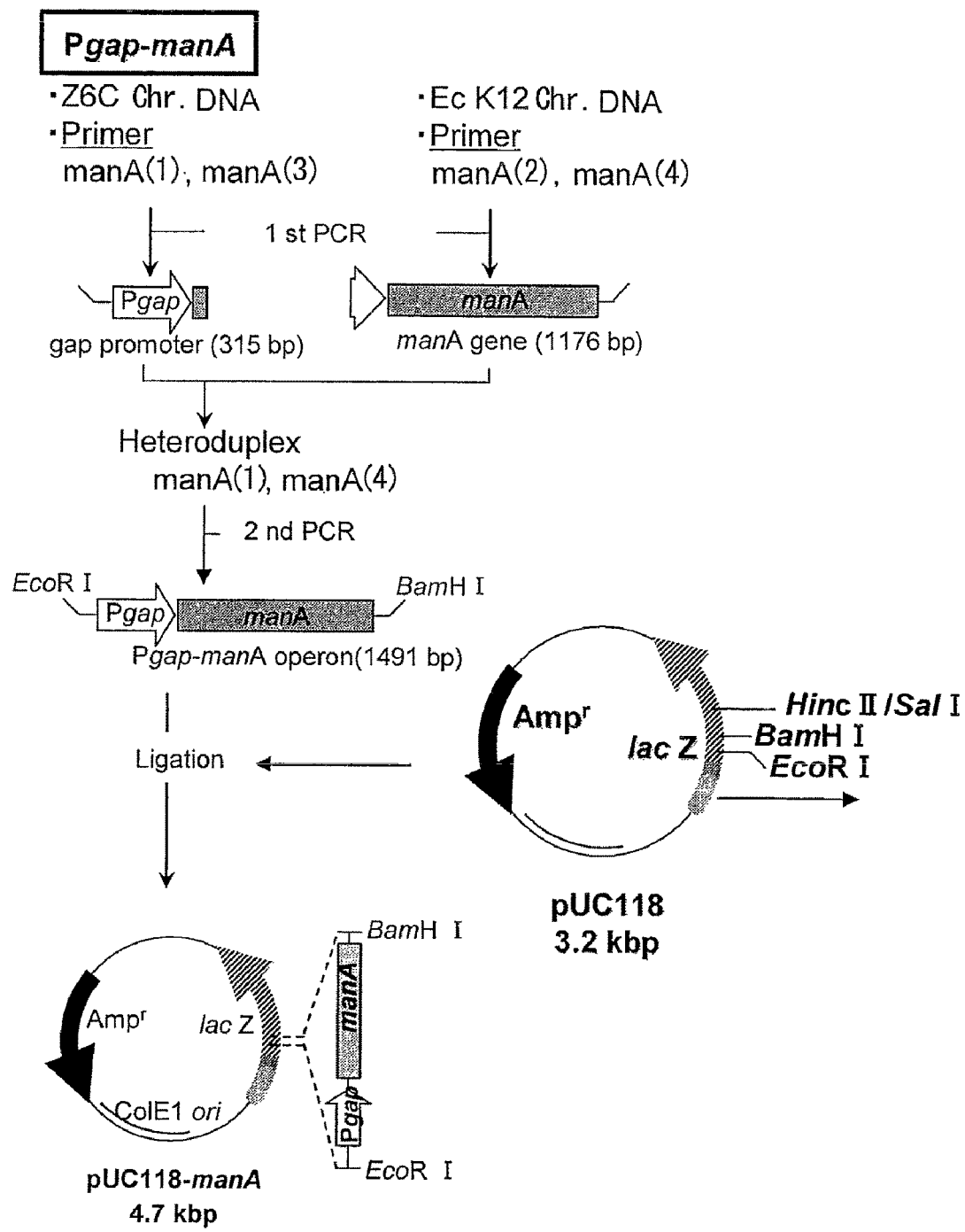
FIG. 2 is a diagram illustrating the procedure for cloning manA of Escherichia coli origin.

FIG. 2 summarizes this cloning operation.

Figure 3:
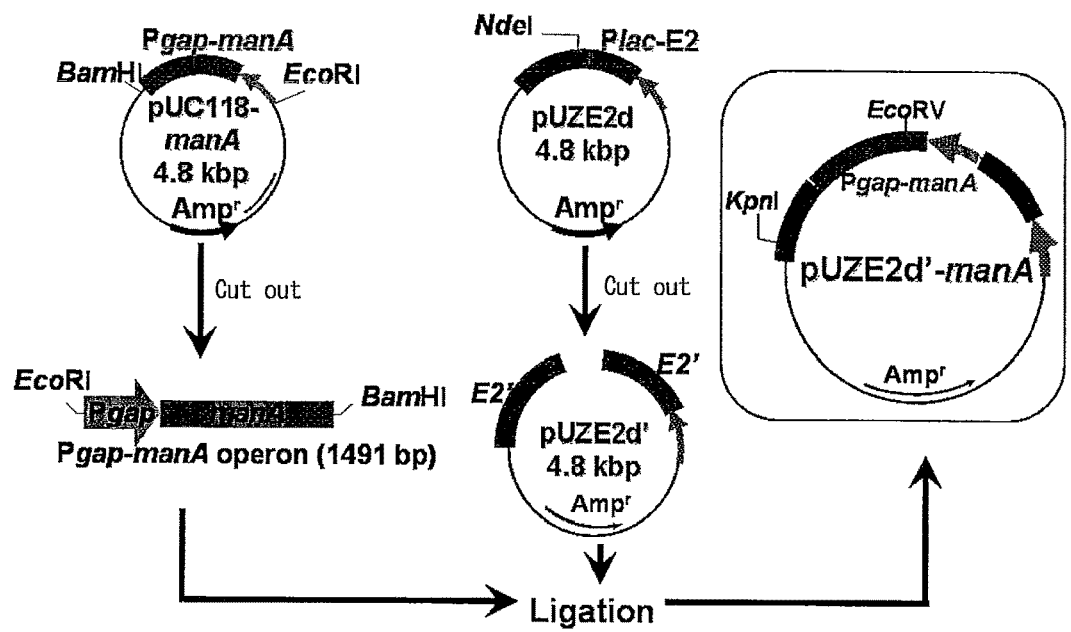
FIG. 3 is a restriction map illustrating the procedure for constructing a recombinant plasmid pUZE2d'-manA for integration of chromosomal DNA.

TABLE 1 manA primers manA(1) (SEQ ID NO: 1):
CGGAATTCGTTCGATCAACAACCCGAATCCTATCG manA(2) (SEQ ID NO: 2):
CTTAATAAGTTAGGAGAATAAACATGCAAAAACTCATTAACTCAGTGCAA manA(3) (SEQ ID NO: 3):
TTGCACTGAGTTAATGAGTTTTTGCATGTTTATTCTCCTAACTTATTAAG manA(4) (SEQ ID NO: 4):
CGCGGATCCTTACAGCTTGTTGTAAACACGCGCTA (2) Construction of Vector pUZE2d'-manA for Chromosomal Integration FIG. 3 is a diagram illustrating the construction of a vector for chromosomal integration by targeting at the E2 site.

Vector pUZE2d (4.8 kb) was treated with NdeI, blunted, and then treated with BAPP to cut out the DNA. Further, Pgap-manA (1.5 kb) was digested from pUC118-manA (4.8 kb) with BamHI and EcoRI, followed by blunting to cut out the manA fragment. Then, ligation was carried out overnight at 4° C. and 16° C. using Ligation High and T4 ligase, and transformation of *E. coli* JM109 strain was carried out by a heat shock method to extract a plasmid. From the extracted plasmid, a manA fragment of 1.5 kbp was confirmed by PCR using manA(1) and manA(4) primers shown in Table 2 which were designed based on a known genomic E2 sequence of *Zm. mobilis* (Biosci. Biotech. Biochem., 59(2), 289-293 (1995); DNA accession number D17524 (DDBJ, EMBL)). Further, when the plasmid was digested with EcoRV and KpnI, a band of a 5.3 kbp fragment was detected, which showed that the fragment was composed of 4.8 kbp and 1.5 kbp fragments being in the forward direction relative to the E2 gene. In view of this result, the plasmid was designated as plasmid pUZE2d'-manA.

TABLE 2

E2 primers

E2(1) (SEQ ID NO: 5):
ACTTAATAAGTTAGGAGAATAAACATGTTGAATAAAGCAGGCATTGCAGA

E2(2) (SEQ ID NO: 6):
GCTCTAGATCATTATTTATTCAATAAAGACAGGGC

E2(3) (SEQ ID NO: 7):
AGCAAATAATTTCTGGGATTTCCGC

E2(4) (SEQ ID NO: 8):
AGGCCGCTCCGTCTGG (3) Confirmation of Integration of manA into Chromosomal DNA of *Zm. mobilis*

A strain producing levansucrase in a large amount which had been derived from *Zm. mobilis* IFO13756 by natural mutation (hereinafter referred to as ZM ms strain) was selected as a host strain, and the transformation of the host strain was carried out by an electroporation method using a high concentration plasmid solution. Then, three successive subcultures were carried out, and the culture was applied on a 2% mannose-RM plate. From the third day after the application, the culture was continued for about two weeks, and a large colony grown therein was arbitrarily selected and inoculated into a 2% mannose-RM liquid medium. Bacterial cells were harvested from a suspension of grown cells, and the cells were washed once with sterilized MilliQ water and then were suspended in 1 mL of sterilized MilliQ water to prepare a sample for DNA extraction. One µL out of 50 µL of the extract was subjected to PCR amplification using manA primers manA(1) and manA(4), and E2 primers E2(1) and E2(2). As a result, a manA fragment (1.5 kbp) was detected in the amplification using the manA primers, and a band was detected at 2.8 kbp in the amplification using the E2 primers. This result showed that manA was inserted at the E2 site on the chromosomal DNA because 2.8 kbp corresponded to the length of the fragment prepared by integrated manA (1.5 kbp) into E2 (1.3 kbp).

The strain ZM ms has been deposited since Aug. 13, 2007 under the Budapest Treaty with the International Patent Organism Depository, National Institute of Advanced Industrial Science and Technology, tsukuba Central 6, 1-1-1 Higashi, Tsukuba 305-8566, Japan, under accession number FERM BP-11024.

Example 2

Giving Simultaneous Fermentation Capacity of Xylose to Bacterial Strain

In order to introduce genes of enzymes in xylose metabolism system of *E coli* origin into *Zm. mobilis*, first, genes of xylA, xylB, tal and tktA were cloned in *E. coli* using vector pUC118, and then inserted into a shuttle vector for *E. coli* and *Zm. mobilis*, pZA22, to construct a recombinant plasmid pZA22-xt. Then, pZA22-xt was introduced into *Zm. mobilis* to which mannose fermentation capacity had been given by integrating manA into the chromosome thereof. Thus, the simultaneous fermentation capacity of glucose, xylose and mannose was given to the strain.

(1) Construction of pUC118-xylAB

The necessary genes were cloned from *E. coli* genomic DNA by PCR. Further, a promoter gene (GAP promoter) for controlling the expression of glyceraldehyde-3-phosphate dehydrogenase, which was reported to be expressed in a large amount in *Zm. mobilis* cells, was used to express the introduced four kinds of enzyme genes in *Zm. mobilis* cells.

A xylose isomerase gene and a xylulokinase gene of *E. coli* origin were cloned by PCR. Namely, 4 types of PCR primers as shown in Table 3 were designed based on a known gene sequence of glyceraldehyde-3-phosphate dehydrogenase of *Zm. mobilis* origin (J. Bacteriol., Vol. 169(12), 5653-5662, 1987) and a known nucleotide sequences of a xylose isomerase gene and a xylulokinase gene of *E. coli* origin (Appl. Environ. Microbiol., vol. 47(1), 15-21, 1984) to prepare a DNA fragment wherein the xylose isomerase gene and the xylulokinase gene of *E. coli* origin were tandemly linked in the downstream of the promoter gene of glyceraldehyde-3-phosphate dehydrogenase gene of *Zm. mobilis* origin, and EcoRI restriction cleavage sites for cloning were provided at both termini of the DNA fragment, respectively.

TABLE 3

XYL primers

XYL1 (SEQ ID NO: 9):
CGGAATTCGTTCGATCAACAACCCGAATCCTATCG

TABLE 3-continued

XYL primers

XYL2 (SEQ ID NO: 10):
TACTGGAATAAATGGTCTTCGTTATGCAAGCCTATTTTGACCAGCCTCGAT

XYL3 (SEQ ID NO: 11):
ATCGACTGGTCAAAATAGGCTTGCATAACGAAGACCATTTATTCCAGTA

XYL4 (SEQ ID NO: 12):
CGGAATTCATGCATAGTTGCCAAAAGTTGCTGTCA

For primary PCR, a DNA fragment of about 300 bp containing the promoter and the N-terminal site of the xylose isomerase gene was amplified by using a genomic DNA prepared from *Zm. mobilis* cells as a template and the primers XYL1 and XYL3. On the other hand, a DNA fragment of about 3.0 kbp containing a part of the promoter gene, the xylose isomerase gene and the xylulokinase gene was amplified by using an *E. coli* genomic DNA as a template and the primers XYL2 and XYL4. Then, the DNA fragment containing the promoter gene and the DNA fragment containing the xylose isomerase gene and the xylulokinase gene were mixed and heated at 94° C. for 20 minutes. The mixture was maintained at 37° C. for 15 minutes to form a heteroduplex. The heteroduplex was allowed to react at 72° C. for 3 minutes in the presence of TaqDNA polymerase. To this reaction mixture, primer XYL1 and primer XYL4 were added and secondary PCR was carried out to amplify a DNA fragment of about 3.2 kbp in which the Gap promoter gene, the xylose isomerase gene and the xylulokinase gene were linked in this order. After the two termini of this DNA fragment was subjected to a blunting reaction, the DNA fragment and a fragment of a vector plasmid DNA for *E. coli*, pUC118, cleaved with HincII restriction enzyme were mixed, followed by linking with T4 ligase to produce a recombinant plasmid DNA. The produced recombinant plasmid was used to transform *E. coli* JM109 according to a conventional method, and then the transformed strain was applied on an LB plate medium (1% Bacto Tripton, 0.5% yeast extract, 1% NaCl, and 1.5% agar) containing 50 µg/mL of ampicillin, 0.1 mM isopropyl-β-D-thiogalactoside and 20 µg/mL of 5-bromo-4-chloro-3-indolyl-β-D-galactopyranoside to form colonies. A recombinant plasmid extracted from the transformed strain which formed a white colony was designated as pUC118-xylAB.

Figure 4:
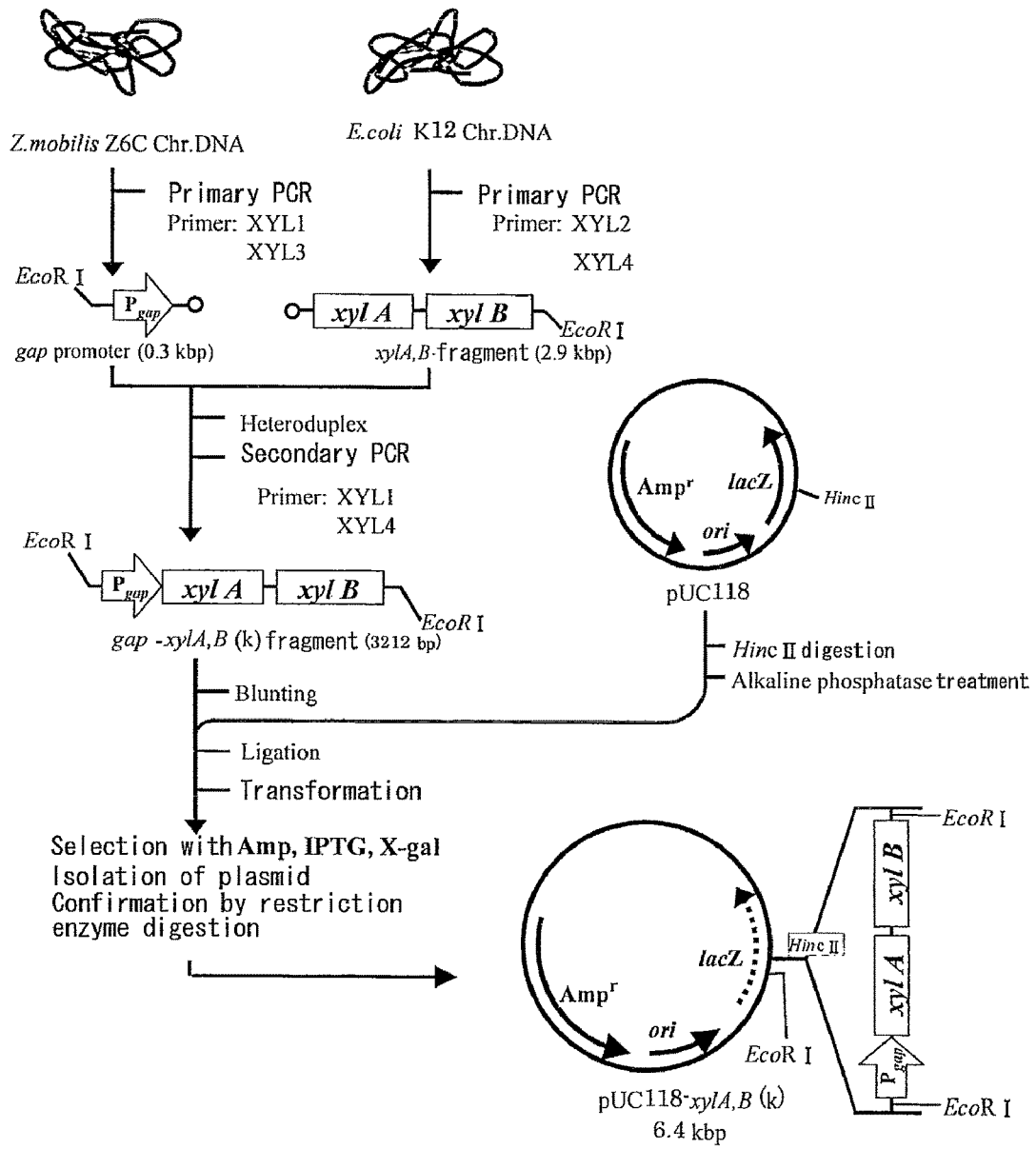
FIG. 4 is a restriction map illustrating the procedure for constructing pUC118-xylAB.

FIG. 4 summarizes this operation.

(2) Construction of pUC118-taltktA

The transaldolase gene and the transketolase gene do not constitute an operon on *E. coli* genomic DNA, and their positions are remote from each other. Therefore, the transaldolase and transketolase were cloned separately, and then were linked so that they were controlled by GAP promoter of *Zm. mobilis* origin. For this purpose, 4 types of PCR primers shown in Table 4 were designed based on a known gene sequence of enolase enzyme of *Zm. mobilis* origin and a known transaldolase gene of *E. coli* origin (Nucleic Acids Res., Vol. 20, 3305-3308, 1992).

TABLE 4

TAL primers

TAL1 (SEQ ID NO: 13):
CGGAATTCTCGAGCTCCAGTTACTCAATACGTAACAATAA

TAL2 (SEQ ID NO: 14):
AAGATTTTAAGAAAGGTTTCGATATGACGGACAAATTGACCTCCCTTCGT

TABLE 4-continued

TAL primers

TAL3 (SEQ ID NO: 15):
ACGAAGGGAGGTCAATTTGTCCGTCATATCGAAACCTTTCTTAAAATCTT

TAL4 (SEQ ID NO: 16):
CATTTTGACTACCAGATCTAGATTACAGCAGATCGCCGATCATTTTTCC

For primary PCR, a genomic DNA prepared from Zm. mobilis cells was used as a template, and primers TAL1 and TAL3 were used to amplify a DNA fragment of about 300 bp containing the promoter and the N-terminal site of the transaldolase gene, and having a XhoI restriction cleavage site added at the upstream terminal of the promoter gene. On the other hand, E. coli genomic DNA was used as a template, and primers TAL2 and TAL4 were used to amplify a DNA fragment of about 1.2 kbp containing a part of a promoter gene and the transaldolase gene, and having a XbaI restriction cleavage site added at the C-terminus of the transaldolase gene. Then, the DNA fragment containing the promoter gene and the DNA fragment containing the transaldolase gene were mixed and the mixture was heated at 94° C. for 20 minutes, and then maintained at 37° C. for 15 minutes to form a heteroduplex. Then, the heteroduplex was allowed to react at 72° C. for 3 minutes in the presence of TaqDNA polymerase. To this reaction mixture, primer TAL1 and primer TAL4 were added and secondary PCR was carried out to amplify a DNA fragment of about 1.3 kbp in which the Eno promoter gene and the transaldolase gene were linked in this order. After the two termini of this DNA fragment was subjected to a blunting reaction, the DNA fragment and a fragment of a vector plasmid DNA for E. coli, pUC118, cleaved with HincII restriction enzyme were mixed, followed by linking with T4 ligase to produce a recombinant plasmid DNA. The produced recombinant plasmid was used to transform E. coli JM109 according to a conventional method, and then the transformed strain was applied on an LB plate medium (1% Bacto Tripton, 0.5% yeast extract, 1% NaCl, and 1.5% agar) containing 50 µg/mL of ampicillin, 0.1 mM isopropyl-β-D-thiogalactoside and 20 µg/mL of 5-bromo-4-chloro-3-indolyl-β-D-galactopyranoside to form colonies. A recombinant plasmid extracted from the transformed strain which formed a white colony was designated as pUC118-tal.

Figure 5:
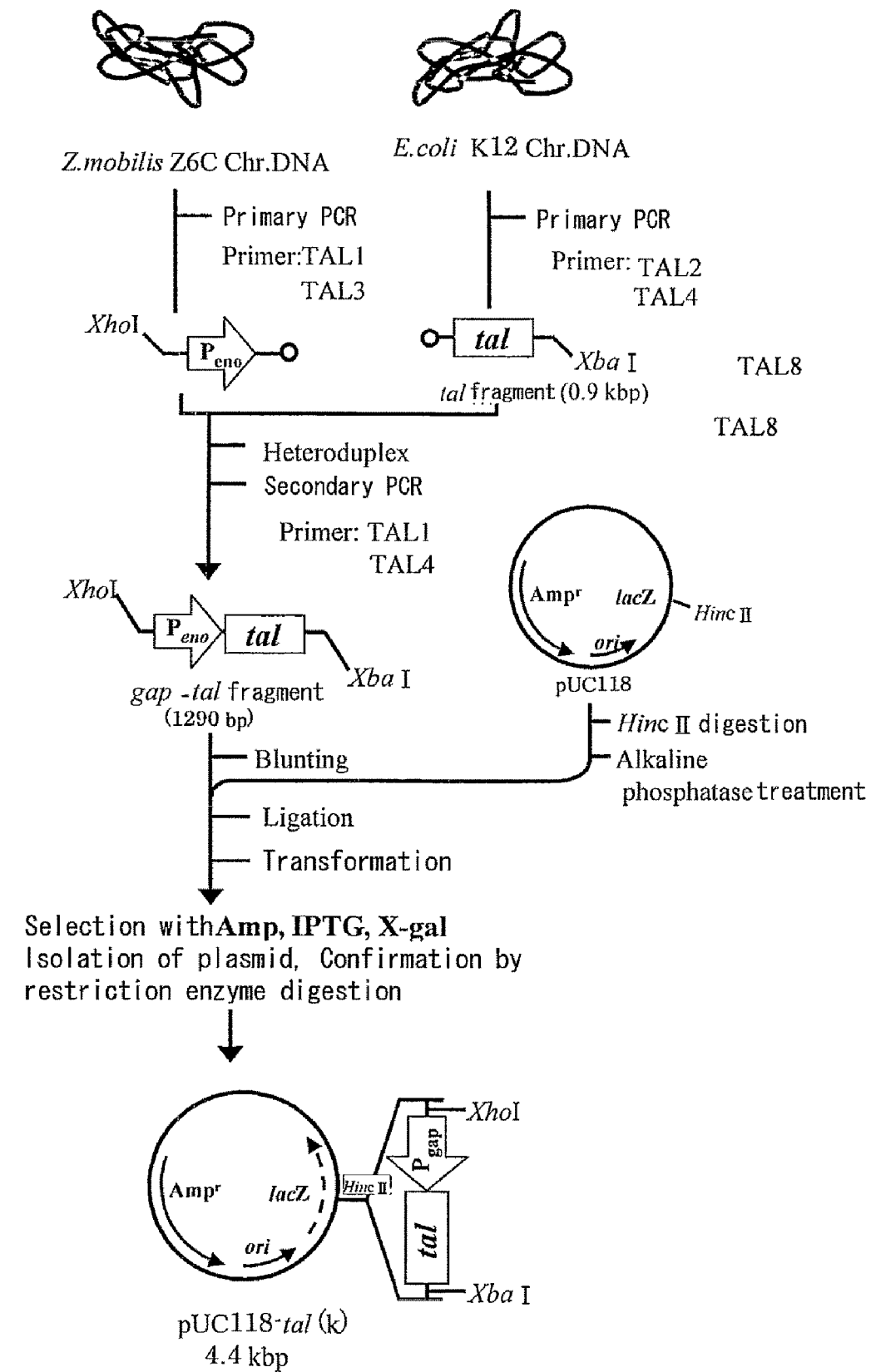
FIG. 5 is a restriction map illustrating the procedure for constructing pUC118-tal.

FIG. 5 summarizes this operation.

Subsequently, amplification of the transketolase gene by PCR was carried out. Two types of primers shown in Table 5 were synthesized based on a known nucleotide sequence of a transketolase gene (J. Bacteriol., Vol. 174, 1707-1708, 1992).

TABLE 5

TKT primers

TKT1 (SEQ ID NO: 17):
CGGAATTCTCGAGCTCCAGTTACTCAATACGTAACAATAA

TKT2 (SEQ ID NO: 18):
CGGCATGCCTCGAGGCAAACGGACATTATCAAGGTAATAAAAAAGGTCGC

For primary PCR, a genomic DNA prepared from E. coli cells was used as a template, and primers TKT1 and TKT2 were used to amplify a DNA fragment of about 2.1 kbp containing an XbaI restriction cleavage site added at the upstream of the N-terminus of the transketolase gene and an XhoI restriction cleavage site added at the downstream of the C-terminus of the transketolase gene. After the two termini of this DNA fragment was subjected to a blunting reaction, the DNA fragment and a fragment of a vector plasmid DNA for E. coli, pUC118, cleaved with HincII restriction enzyme were mixed, followed by linking with T4 ligase to produce a recombinant plasmid DNA. The produced recombinant plasmid was used to transform E. coli JM109 according to a conventional method, and then the transformed strain was applied on an LB plate medium (1% Bacto Tripton, 0.5% yeast extract, 1% NaCl, and 1.5% agar) containing 50 µg/mL of ampicillin, 0.1 mM isopropyl-β-D-thiogalactoside and 20 µg/mL of 5-bromo-4-chloro-3-indolyl-β-D-galactopyranoside to form colonies. A recombinant plasmid extracted from the transformed strain which formed a white colony was designated as pUC118-tkt.

Figure 6:
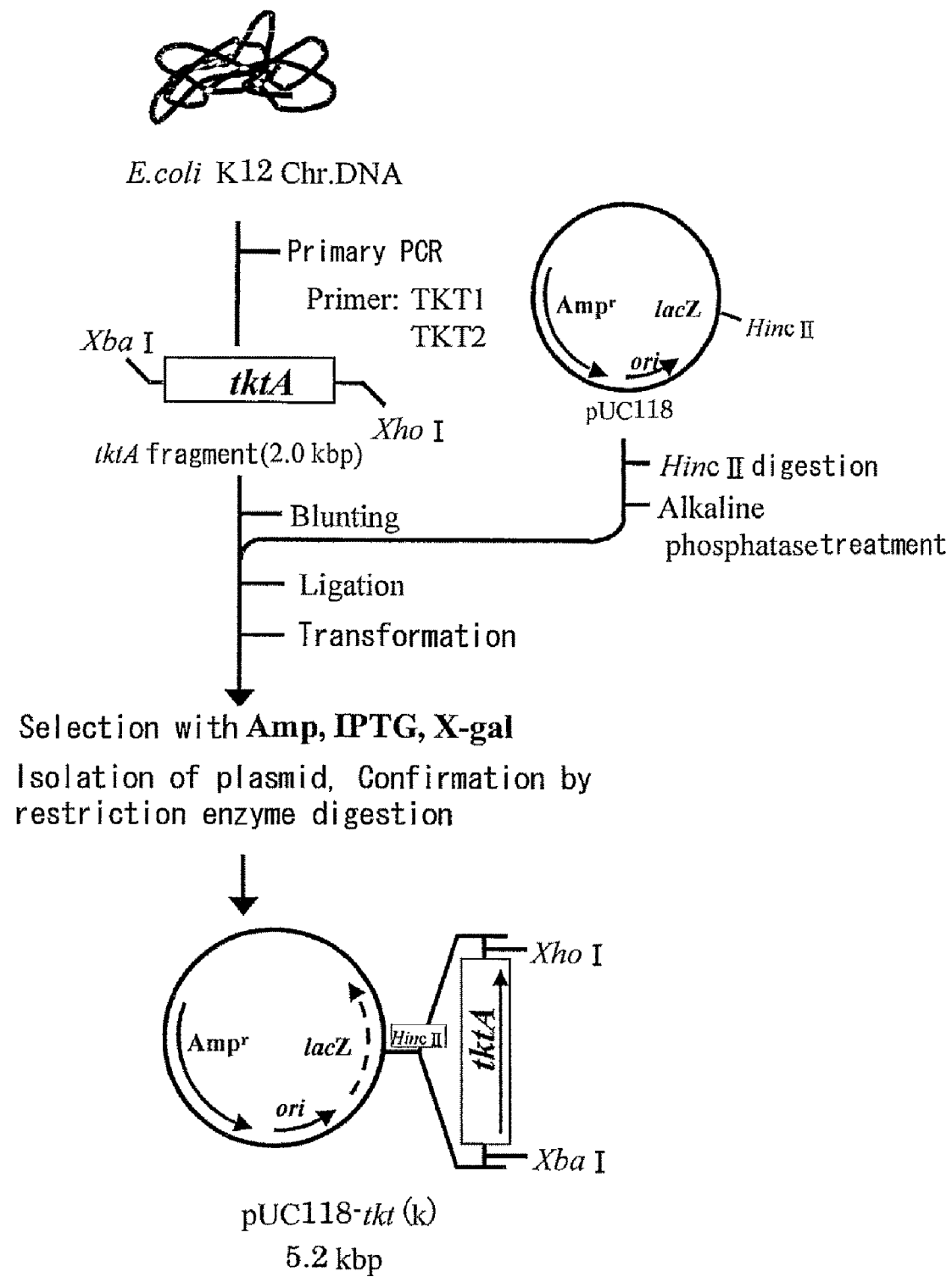
FIG. 6 is a restriction map illustrating the procedure for constructing pUC118-tkt.

FIG. 6 summarizes this operation.

Subsequently, a recombinant plasmid containing a DNA fragment in which GAP promoter gene, the transaldolase gene and the transketolase gene were linked was produced. Namely, a DNA fragment obtained by cleaving the recombinant plasmid pUC118-tal at the XbaI restriction cleavage site and the SphI restriction cleavage site present in the downstream region of the C-terminus of the transaldolase gene, and a DNA fragment of about 2.1 kbp containing a transketolase gene prepared by cleaving the recombinant plasmid pUC118-tkt with XbaI and SphI were mixed, followed by linking with T4 ligase to produce a recombinant plasmid DNA. The produced recombinant plasmid was used to transform E. coli JM109 according to a conventional method, and then the transformed strain was applied on an LB plate medium (1% Bacto Tripton, 0.5% yeast extract, 1% NaCl, and 1.5% agar) containing 50 µg/mL of ampicillin to form colonies. It was confirmed that a recombinant plasmid extracted from the transformed strain which formed a colony had Eno promoter gene, transaldolase gene and transketolase gene tandemly linked in this order, and this recombinant plasmid was designated as pUC118-tal+tkt.

Figure 7:
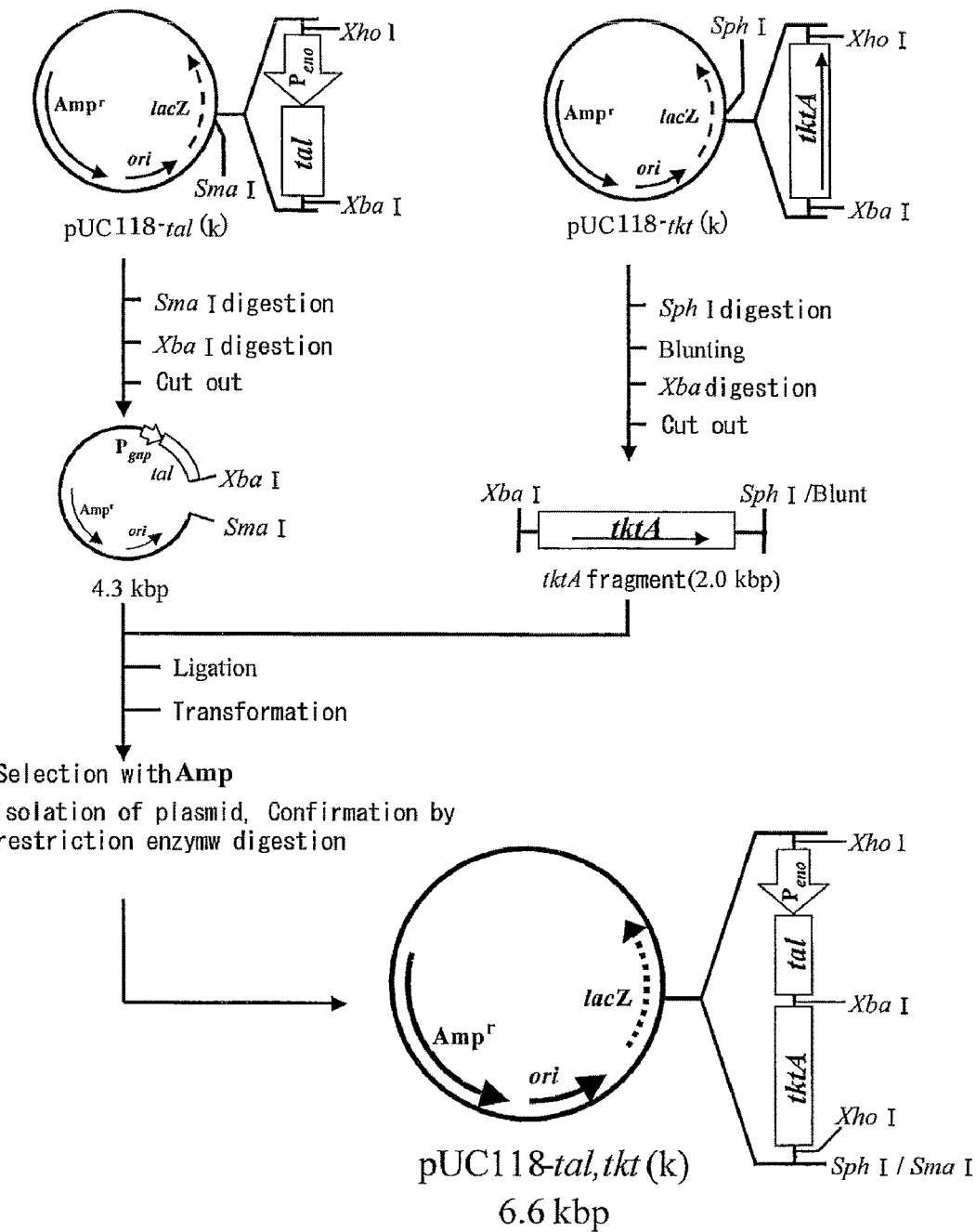
FIG. 7 is a restriction map illustrating the procedure for constructing pUC118-tal+tkt.

FIG. 7 summarizes this operation.

(3) Construction of pZA22-xy

In order to introduce genes of 4 kinds of enzymes of xylose metabolism system into Zm. mobilis and express them therein, these genes were inserted into a shuttle vector to produce a recombinant plasmid. A DNA fragment of about 3.3 kbp containing Eno promoter gene, transaldolase gene and transketolase gene was produced by cleaving the recombinant plasmid pUC118-taltkt with XhoI restriction enzyme. This fragment and a shuttle vector pZA22 cleaved by restriction enzyme SalI were mixed, followed by linking with T4 ligase to produce a recombinant plasmid. The produced recombinant plasmid was used to transform E. coli JM109 according to a conventional method, and then the transformed strain was applied on an LB plate medium (1% Bacto Tripton, 0.5% yeast extract, 1% NaCl, and 1.5% agar) containing 50 µg/mL of chloramphenichol to form colonies. It was confirmed that a recombinant plasmid extracted from the transformed strain which formed a colony had Eno promoter gene, transaldolase gene and transketolase gene linked in this order. On the other hand, a DNA fragment was prepared by cleaving pUC118-xylAxylB with EcoRI restriction enzyme to cut out a DNA fragment of about 3.4 kbp containing Gap promoter gene, xylose isomerase gene and xylulokinase gene, and blunting the two cleaved termini. Then, the prepared DNA fragment and a product obtained by cleaving pZA22 recombinant plasmid, which had been prepared by inserting a transaldolase gene and a transketolase gene, with EcoRV restriction enzyme were mixed, followed by linking with T4 ligase to produce a recombinant DNA plasmid. The produced recombinant plasmid was used to transform E. coli JM109 according to a conventional method, and then the transformed strain was applied on an LB plate medium (1% Bacto Tripton, 0.5% yeast extract, 1% NaCl, and 1.5% agar) containing 50 μg/mL of chloramphenicol to form colonies. It was confirmed that a recombinant plasmid extracted from the transformed strain which formed a colony had GAP promoter, xylose isomerase, xylulokinase gene, Eno promoter, transaldolase gene and transketolase gene linked in this order, and this recombinant plasmid was designated as pZA22-xt.

Figure 8:
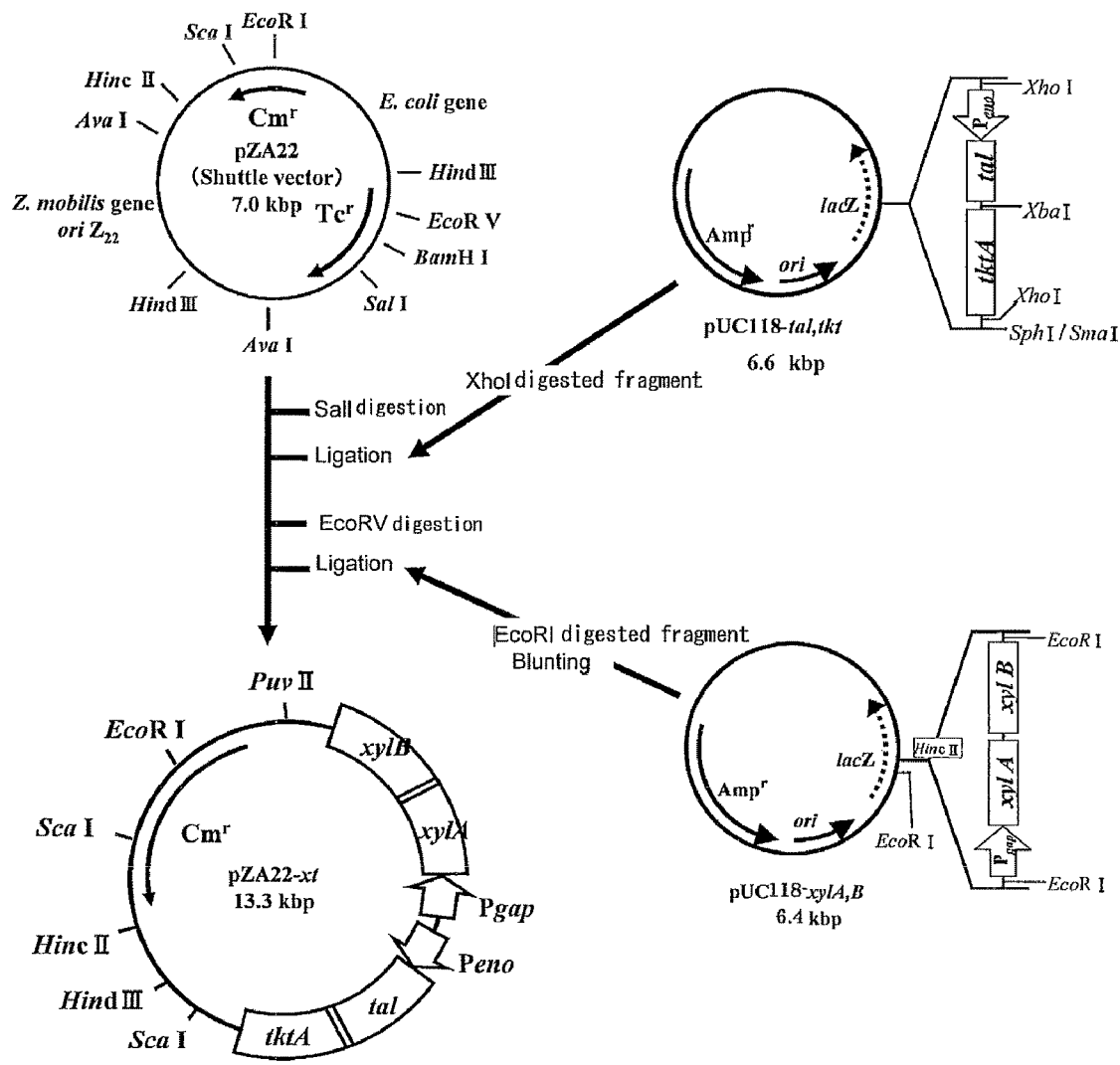
FIG. 8 is a restriction map illustrating the procedure for constructing pZA22-xt.

FIG. 8 summarizes this operation.

(4) Giving Xylose Fermentation Capacity to Zm. mobilis

The recombinant plasmid pZA22-xt having xylAB and taltktA genes tandemly inserted into plasmid pZA22 was used to study breeding of a strain having xylose fermentation capacity.

The operation is as follows. The recombinant plasmid pZA22-xt was used to transform Zm. mobilis IFO13756 according to a conventional method, and the transformed strain was selected by applying on a glucose-RM plate medium (2% glucose, 1.0% yeast extract, 0.2% KH2PO4, 1.5% agar, and 100 μg/mL chloramphenicol, pH 6.0). A transformed strain which had formed a colony was inoculated into xylose-RM medium (2% xylose, 1.0% yeast extract, 0.2% KH2PO4, and 100 μg/mL chloramphenicol, pH 6.0) to study its growth based on xylose as a carbon source and the fermentation capacity for the production of ethanol. However, the transformed strain exhibited only feeble growth in the xylose-RM medium, and did not exhibit the fermentation capacity for producing ethanol. Then, Zm ms described above was selected as a host strain and transformed with pZA22-xt to obtain Zm ms[pZA22-xt] strain. ZM ms[pZA22-xt] strain grown in a glucose-RM plate medium was inoculated into a xylose-RM medium to study its growth based on xylose as a carbon source and the fermentation capacity for producing ethanol. As a result, it was confirmed that Zm ms[pZA22-xt] strain grew based on xylose as a carbon source.

Figure 9:
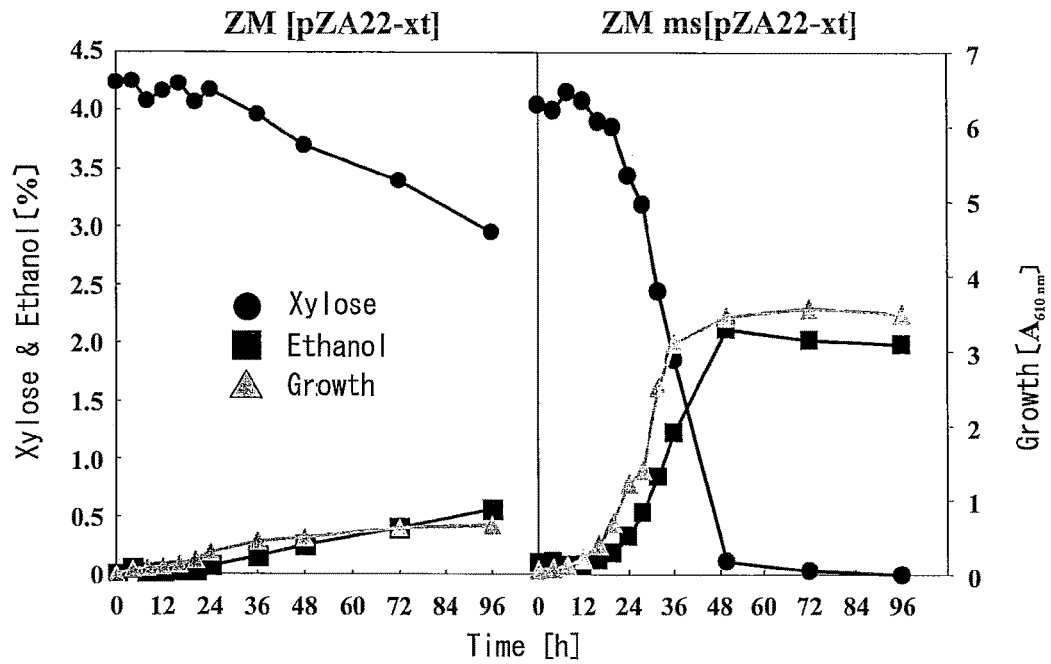
FIG. 9 is a graph illustrating the results of the fermentation test of xylose in Example 2(4).

A fermentation test of ZM ms[pZA22-xt] strain was carried out in a 4% xylose medium. As a control, a strain obtained by introducing pZA22-xt into a wild strain with (ZM[pZA22-xt]) was subjected to the fermentation test. ZM ms[pZA22-xt] strain completely utilized 4% xylose in 48 hours to produce ethanol in the theoretical yield. On the other hand, in ZM [pZA22-xt] strain, degradation of only a part of xylose due to feeble growth was observed, while no fermentation capacity for producing ethanol was found (FIG. 9).

Example 3

Giving Simultaneous Fermentation Capacity of Glucose, Mannose and Xylose to Bacterial Strain Simultaneous fermentation capacity of mannose and glucose had been successfully given to Zm. mobilis by integrating manA into the chromosomal DNA thereof. Then, a further study was made to give xylose simultaneous fermentation capacity.

Figure 10:
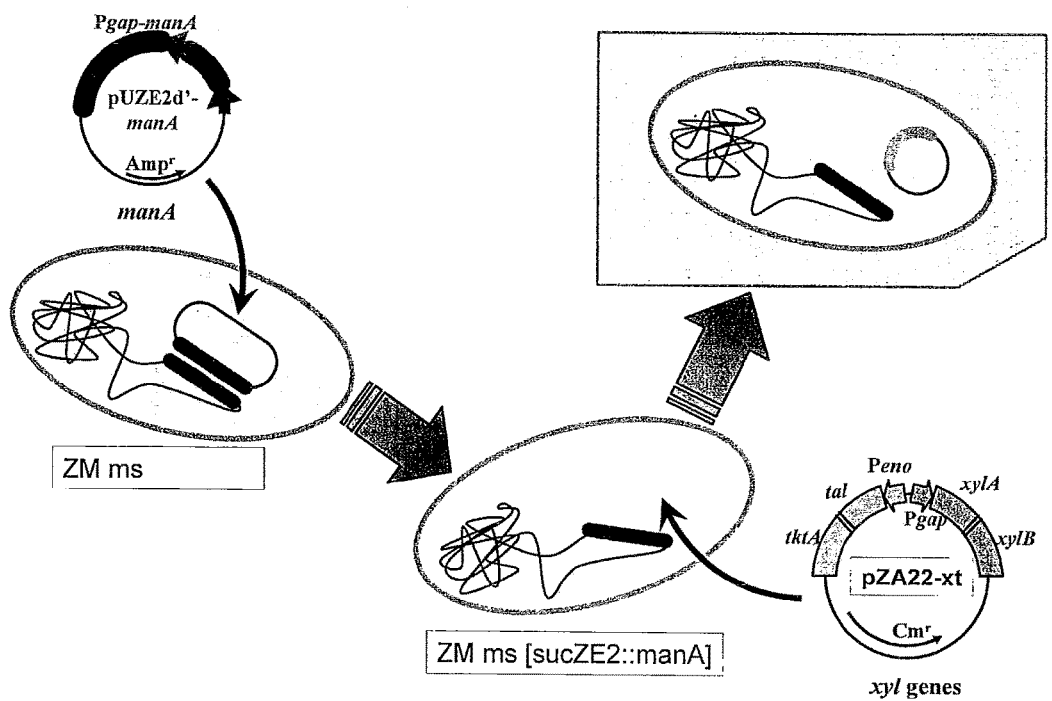
FIG. 10 is a diagram illustrating the procedure for giving simultaneous fermentation capacity of glucose, mannose and xylose to the bacterial strain.

(1) Construction of Strain Having Both Genes of Xylose Metabolism System and Mannose Metabolism System of E. coli Origin Together Competent cells of ZM ms[E2:manA] having manA integrated into the chromosome obtained in Example 1 were prepared, and the cells were transformed with pZA22-xt (FIG. 10). A transformed strain was selected based on the colony formation on a xylose plate medium. Then, growth of obtained colonies in a liquid medium containing xylose and mannose as carbon sources was monitored. A transformed strain which exhibited high growth in both carbon sources of xylose and mannose was selected and used for a fermentation test.

(2) Expression of Genes of Xylose Metabolism System and Mannose Metabolism System in Bred Strain The expression of genes of xylose metabolism system and mannose metabolism co-existing in the strain to be used for a fermentation test was studied. Although endogenous fructokinase activity was found in a wild Zm. mobilis strain, the enzymatic activities of a xylose isomerase, a xylulokinase, a transaldolase and a phosphomannose isomerase were not found therein. However, the expression of phosphomannose isomerase activity was confirmed in ZM ms[E2::manA] strain, and the expression of xylulokinase and transaldolase activities which was the expression indicator of the introduced genes of xylose metabolism system was confirmed in Zm ms[pZA22-xt]. Further, the expression of the genes of xylose metabolism system and manA gene was confirmed in the co-expressing strain and it was also confirmed that the expression level of these genes was higher in these strains as compared with E. coli. Namely, it was confirmed that the introduced genes were stabilized and expressed efficiently.

Table 6 shows the results of confirmation of the introduced gene expression.

TABLE 6

| Bacterial strain | C source | Activity (U/mg) | | |
|---|---|---|---|---|
| | | XK[1] | TA[2] | PMI[3] |
| E. coli JM109 | — | 0.141 | 0.259 | 0.198 |
| ZM ms E2::manA | Mannose | 0 | 0 | 2.666 |
| ZM ms/pZA22-xt | Xylose | 0.907 | 2.915 | 0.036 |
| ZM ms E2::manA/pZA22-xt | Xylose | 1.179 | 2.597 | 1.631 |

Remarks
[1] XK: xylulokinase, 1 U = enzymatic activity to reduce 1 μmol of NADH in one minute
TA: transaldolase, 1 U = enzymatic activity to reduce 1 μmol of NADH in one minute
PMI: phosphomannose isomerase, 1 U = enzymatic activity to produce 1 μmol of NADPH in one minute (3) Fermentation Test of Mixed Sugars of Three Kinds (Under Conditions of Batch-Type Fermentation)

Figure 11A:
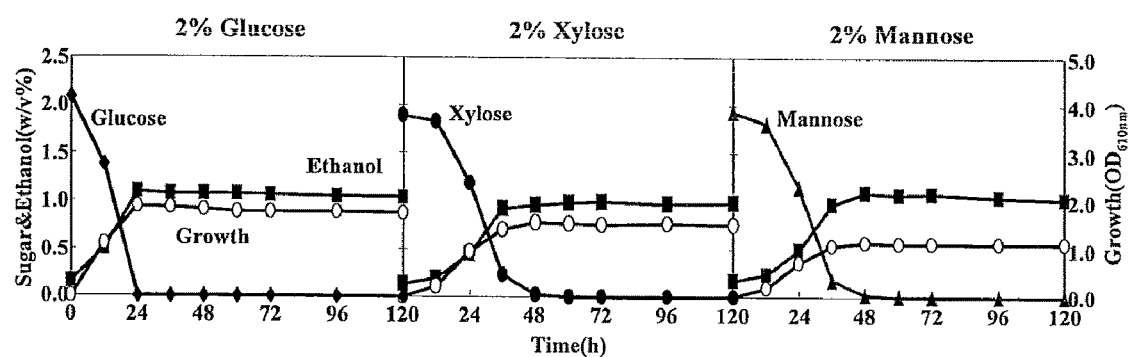
FIG. 11a is a graph illustrating the results of the fermentation test of the bred strain in Example 3.
Figure 11B:
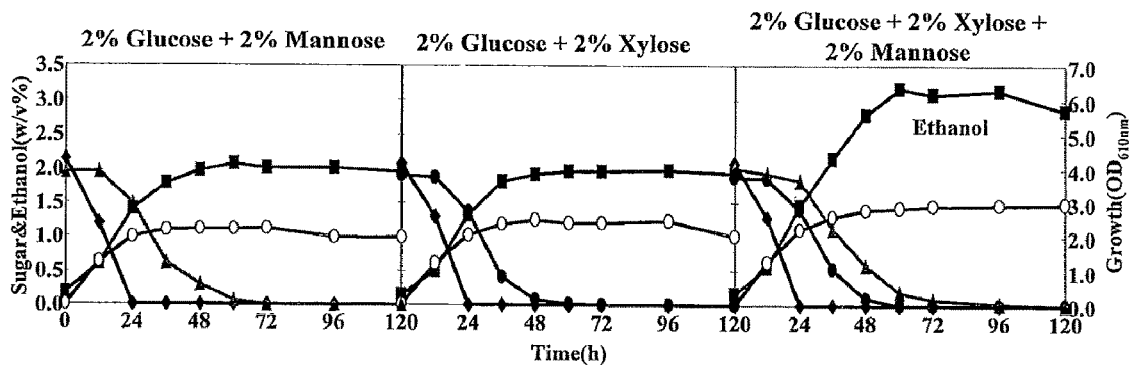
FIG. 11b is a graph illustrating the results of the fermentation test of the bred strain in Example 3.

Fermentation capacity was evaluated by using a bred strain in which manA was introduced into the chromosome and xylA, xylB, tal and tktA were introduced as plasmids. As shown in FIG. 11a and FIG. 11b, when 2% glucose, xylose or mannose was used as a sole carbon source, a slight decrease was recognized as compared with the fermentation rate of glucose, but the strain exhibited a growth conforming to the rapid consumption of xylose and mannose, and ethanol production in the theoretical yield. The strain also exhibited rapid ethanol production with respect to xylose or mannose in the co-presence of glucose. As to the sugar consumption in the co-presence of glucose, xylose and mannose, consumption of glucose occurred first, and then consumption of xylose and mannose occurred in this order. Thus, ethanol production in the theoretical yield was recognized.

As described above, Zm. mobilis strain capable of efficiently converting main sugars contained in an acid-treated saccharified solution, glucose, xylose and mannose, into ethanol has been successfully bred.

The bred strain was designated as ZM m×42, and has been deposited since Aug. 13, 2007, under the Budapest Treaty, with the International Patent Organism Depository, National Institute of Advanced Industrial Science and Technology, tsukuba Central 6, 1-1-1 Higashi, Tsukuba 305-8566, Japan, under accession number FERM BP-11025.

Example 4

Fermentation Test of Acid-Treated Saccharified Solution of Waste Wood

Under Conditions of Batch Type Fermentation

A fermentation test of the bred strain (ZM ms42 [sucZE2::manA, pZA22-xt]) was carried out by using a acid-treated saccharified solution of waste wood. A concentrated sulfuric acid-treated saccharified solution of construction waste materials prepared according to a conventional method (Applied Biochemistry and Biotechnology, Vol. 98-100, 899-807, 2002) was used as the acid-treated saccharified solution of waste wood.

A fermentation test was carried out in the case of adding one volume of 2-fold concentration RM medium (2% of C source, 1% of yeast extract, and 0.2% of $KH_2PO_4$, pH 6.0-6.5) to one volume of the acid-treated saccharified solution, or in the case of adding one volume of 10-fold concentration RM medium to 9 volume of the acid-treated saccharified solution.

Figure 12A:
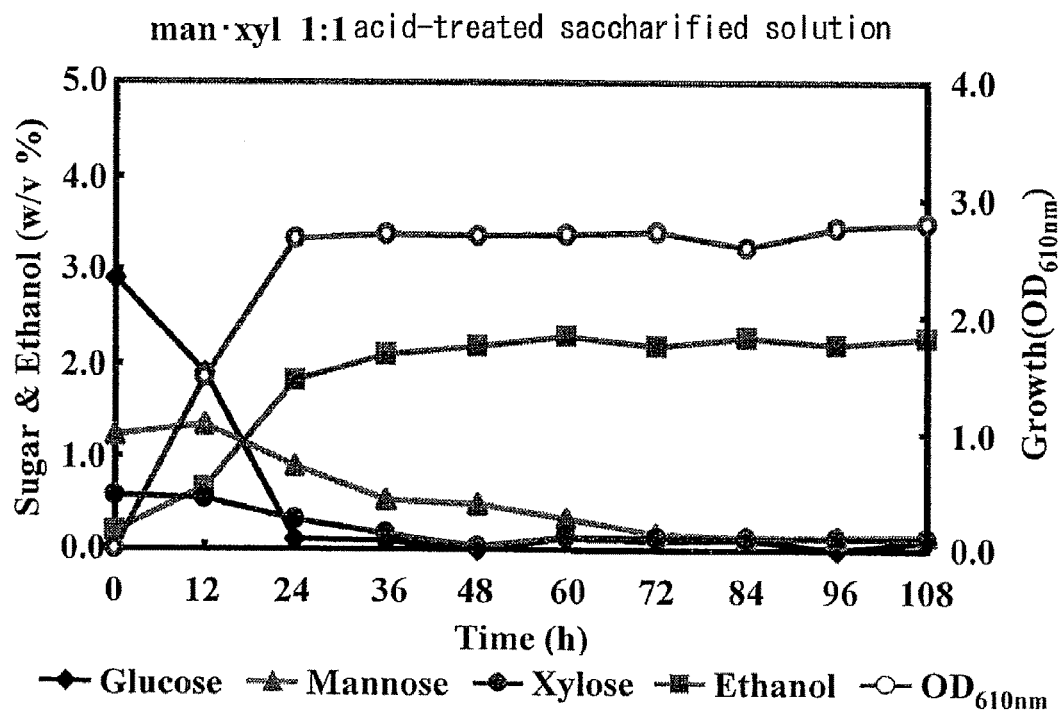
FIG. 12a is a graph illustrating the results of the fermentation test of the waste wood saccharified solution in Example 4.
Figure 12B:
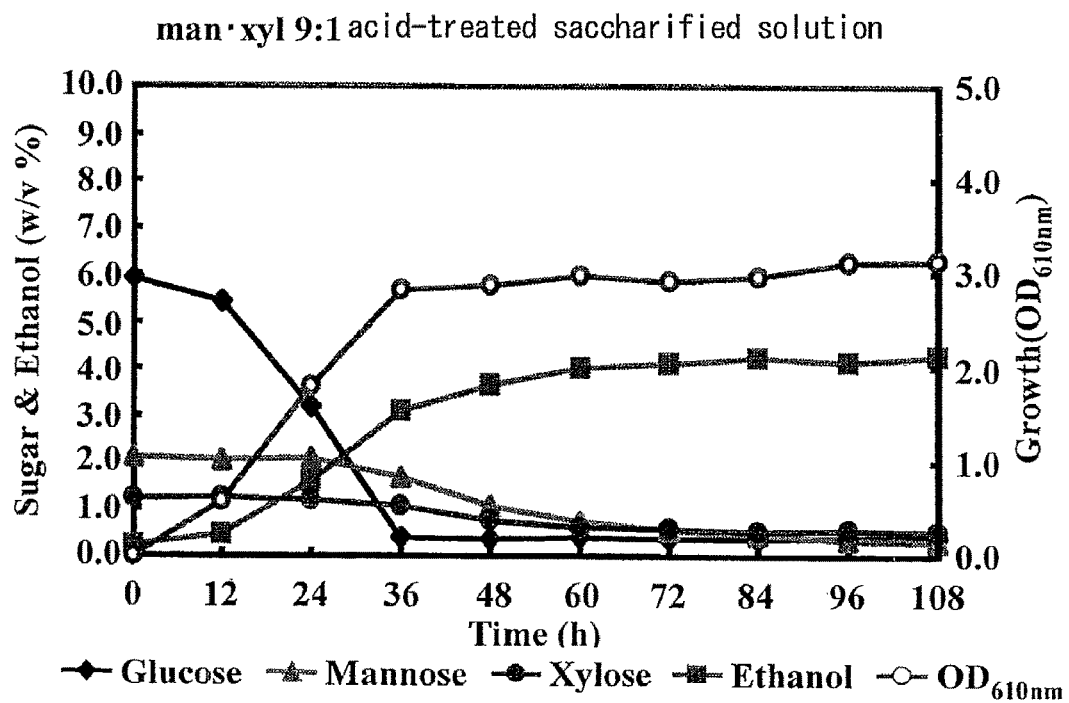
FIG. 12b is a graph illustrating the results of the fermentation test of the waste wood saccharified solution in Example 4.

The results are shown in FIG. 12a and FIG. 12b. According to FIG. 12a, glucose, mannose and xylose were consumed to produce ethanol at a yield close to the theoretical yield. In the case of an acid-treated saccharified solution which was almost an undiluted solution, as shown in FIG. 12b, ZM ms[pZA22-xt] also rapidly fermented the three kinds of sugars to produce ethanol in a high yield.

Example 5

Bioethanol Production Reactor (1) Preparation of Attached Immobilized Bacterial Cell Culture and Reactor The preparation of an attached immobilized bacterial cell culture and production of a reactor for fermentation packed with the bacterial cells are illustrated below.

(a) Preparation of Acid-Treated Saccharified Solution Medium

1) An acid-treated saccharified solution (about pH 1.0) was neutralized to near pH 5.5 with $CaCO_3$.

2) A precipitate was removed from the neutralized acid-treated saccharified solution by suction filtration and the solution was stored at 4° C.

3) The acid-treated saccharified solution was pasteurized at 80° C. for one day or more and, at the same time, an excess precipitate was deposited.

4) For using as a medium for a continuous fermentation test and a fermentation test, RM medium and T-medium, free of C source, were prepared at 2-fold, 2.5-fold and 10-fold concentrations, and each of the media was mixed with the pasteurized acid-treated saccharified solution. Any precipitate formed was removed by centrifugation (25° C., 8000 rpm, 60 minutes).

The T-medium is a medium having a composition of 2% C source, 1% of yeast extract, 1% of $KH_2PO_4$, 0.2% of $(NH_4)_2SO_4$, and 0.05% of $MgSO_4 \cdot 7H_2O$ (pH 6.0).

(b) Preparation of Attached Immobilized Bacterial Cell Culture

1) For culturing in a large scale, the carrier shown in Table 7 was added to 500 ml of RM medium (T-medium) supplemented with appropriate sugars, and the mixture was autoclaved.

TABLE 7

| Name of carrier | Harvested amount | Carrier Diameter |
|---|---|---|
| SIRAN | 20 g | 2-3 mm |
| Purified diatomaceous earth | 13 g | 3-5 mm |

2) After the mixture was cooled to room temperature, the bacterial cells were inoculated into this medium and subjected to stationary culture at 30° C. for 2 days or more. At this time, the carrier having the bacterial cells attached thereto was used as immobilized cells.

(d) Continuous Fermentation Test Using Reactor

A column was packed with 70% of the immobilized bacterial cell culture, and a fluid bath type reactor was used in an ascending method.

Figure 13:
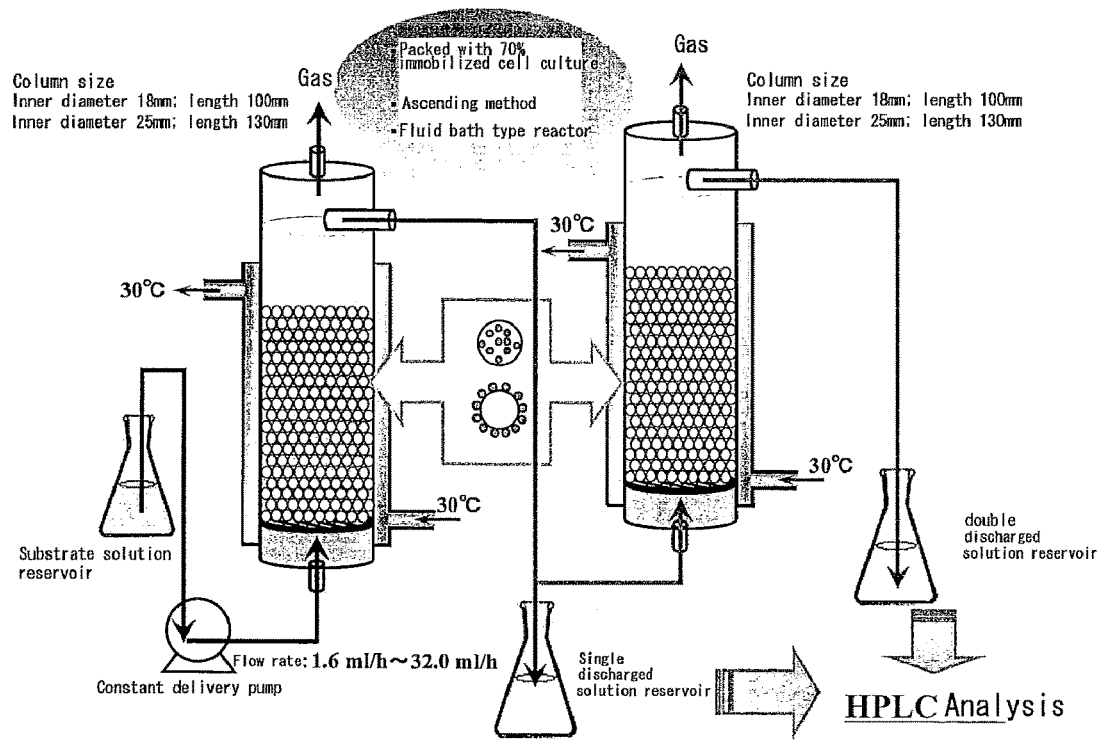
FIG. 13 is a schematic diagram of a reactor illustrating the conditions for continuous fermentation in Example 5.

FIG. 13 and Table 8 show a schematic diagram of the reactor and the conditions for continuous fermentation, respectively.

TABLE 8

| Column size | Flow rate (ml/hour) | Temperature of thermostat (° C.) |
|---|---|---|
| Inner diameter: 25 mm Length: 130 mm | 16, 32 | 30 |
| Inner diameter: 25 mm Length: 260 mm | 13, 16 | 30 |

(c) Method for Analyzing Fermented Solution

Sugar and Ethanol

The production of ethanol and reduction of sugar components were analyzed by using the eluate from the reactor sampled with time. Namely, 1 mL of the column extract was centrifuged (4° C., 15000 rpm, 15 minutes) and was analyzed by HPLC.

The HPLC analysis conditions are as follows.

Condition 1
Column used: BIO-RAD Aminex HPX-87P
Flow rate: 0.4 mL/min
Column temperature: 80° C.
Extraction solution: Degassed distilled water
Sample amount: 5 µL
Condition 2
Column used: Shodex SUGAR KS-801
Flow rate: 0.5 mL/min
Column temperature: 50° C.
Extraction solution: Degassed distilled water
Sample amount: 5 µL The yield of ethanol was determined from the following reaction schemes.

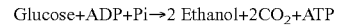

Glucose+ADP+Pi→2 Ethanol+2$CO_2$+ATP

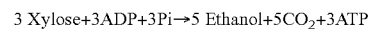

3 Xylose+3ADP+3Pi→5 Ethanol+5$CO_2$+3ATP

Theoretical ethanol yield=0.51% ethanol/% glucose or xylose

Example 6

Figure 14:
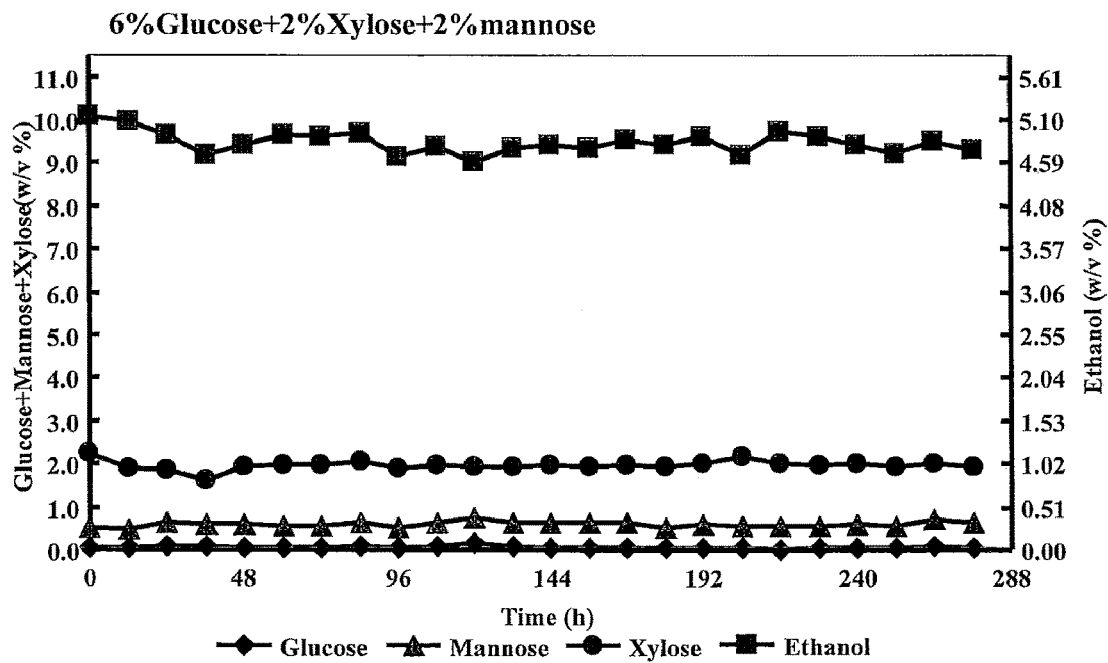
FIG. 14 is a graph illustrating the results of continuous fermentation of the model acid-treated saccharified solution in Example 6.
Figure 15:
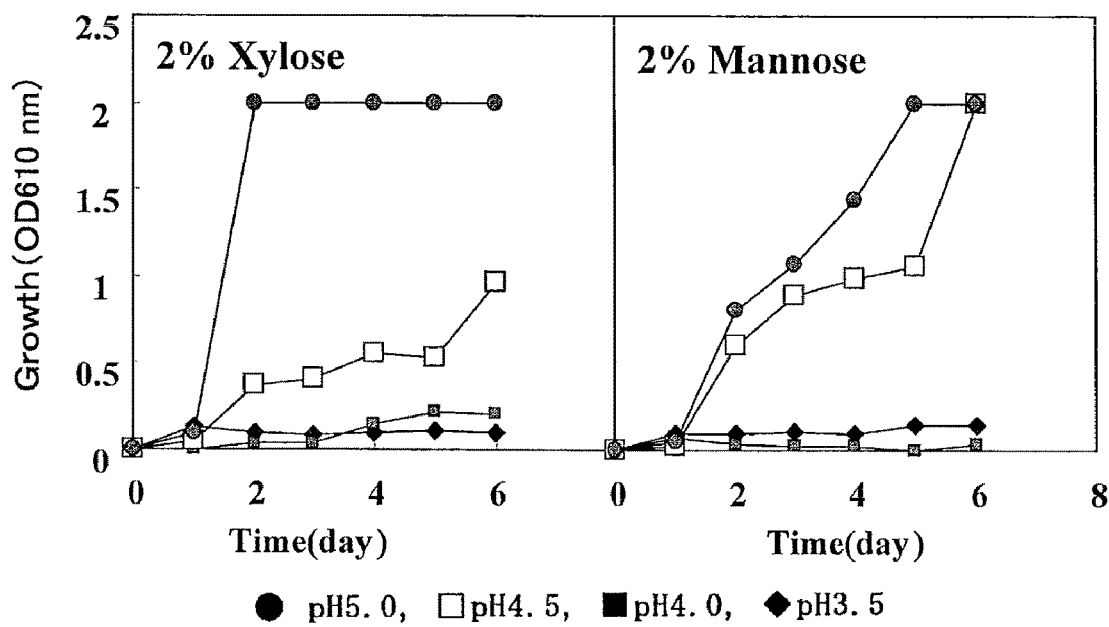
FIG. 15 is a graph illustrating the influence of the initial medium pH in the continuous fermentation of the model acid-treated saccharified solution in Example 6.

Continuous Fermentation of Acid-Treated Saccharified Solution of Waste Wood (1) Continuous Fermentation of Model Acid-Treated Saccharified Solution A reactor packed with the immobilized bacterial cell culture of the recombinant *Zymomonas* as described in Example 5 was used to evaluate continuous fermentation for producing ethanol from a model sugar solution containing glucose, mannose and xylose as a mixture. First, a continuous fermentation test in a reactor packed with ZM ms42 [sucZE2::manA, pza22-xyl] was carried out with a model sugar solution of 6% glucose+2% mannose+2% xylose at 30° C. and pH 6.5 with D=0.2/hour. As a result, as shown in FIG. 14, the production of ethanol in the theoretical yield, which corresponded to the complete consumption of glucose and mannose, was observed. However, xylose was recognized in the fermented solution as a residual sugar, and thus it was found that continuous simultaneous fermentation of three kinds of sugars was difficult. Thus, a cause of the lowered fermentation capacity of xylose was studies, and it was found that the pH of the fermented solution affected the fermentation capacity of xylose. FIG. 15 shows the results obtained by observing the relationship between the fermentation capacity of sugars of the bred strain and the initial pH of the fermented solution. In the case of ZM ms42 [sucZE2::manA, pza22-xyl], the influence of the initial pH on the fermentation of glucose and mannose was not recognized, while it was found that the initial pH of the sugar solution markedly affected the xylose fermentation capacity. Namely, a decrease in the xylose fermentation capacity was observed at pH 5 or lower. These results suggest that pH control is necessary in the continuous fermentation of a mixed sugar solution.

(2) Continuous Fermentation of Acid-Treated Saccharified Solution of Waste Wood

Figure 16:
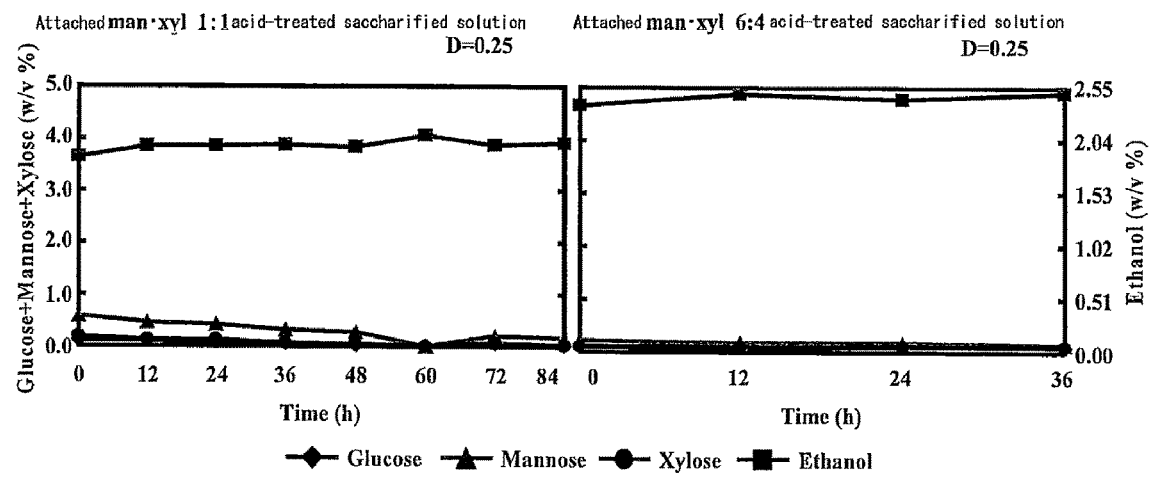
FIG. 16 is a graph illustrating the results of continuous fermentation of the waste wood acid-treated saccharified solution in Example 6.

Continuous ethanol production of diluted acid-treated saccharified solution:

The preparation of immobilized bacterial cell culture of ZM ms42 [sucZE2::manA, pza22-xyl] was carried out according to an attached immobilization method as described above, and a column (inner diameter: 25 mm, length 130 mm) was packed with the bacterial cells while preventing air bubbles from entering. Subsequently, a 1:1 acid-treated saccharified solution-RM medium (pH 6.5) was prepared as described above and continuous fermentation was carried out using this medium at a flow rate of 16 mL/hour and D=0.25/hour in a thermostat at 30° C. The results are shown in FIG. 16*a*.

As shown from these results, although mannose was remaining as a residual sugar at the beginning of fermentation, eventually there was almost no residual sugar. The average ethanol concentration was 1.97%, the yield was 88.79%, and the rate of ethanol formation was 5.18 g/L·hour. From this, the production of ethanol was achieved in a yield close to the theoretical yield.

Then, a continuous fermentation test was carried out according to the same manner except that the sugar concentration was increased. As seen from the results of FIG. 16*b*, there was no residual sugar, and the average ethanol concentration was 2.45%, while the yield was 96.16%, and the rate of ethanol formation was 6.24 g/L·hour. From this, ethanol was produced in the theoretical yield.

(3) Continuous Ethanol Production from Acid-Treated Saccharified Solution

The above results clearly showed that it was possible to produce ethanol by the continuous fermentation of an acid-treated saccharified solution of construction waste materials. Thus, the continuous ethanol production from an acid-treated saccharified solution was studied by a practical test.

Figure 17:
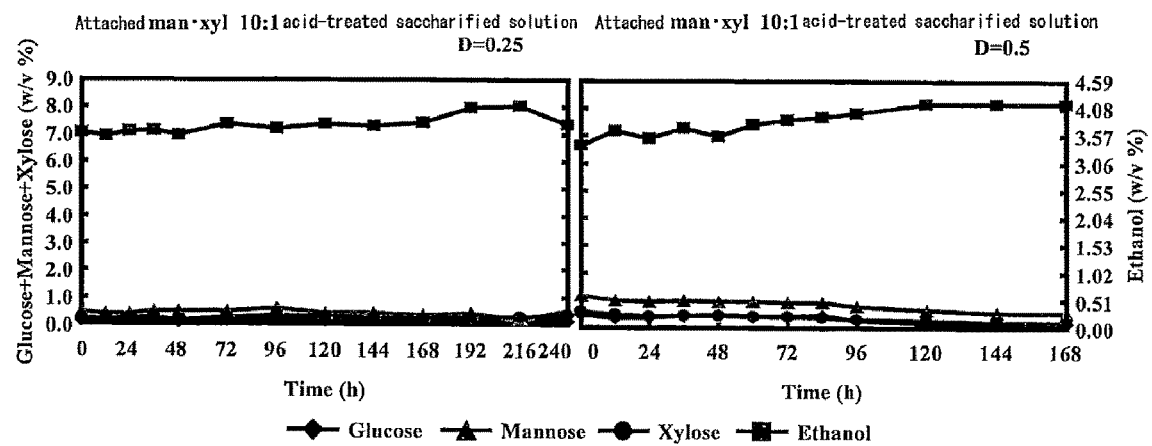
FIG. 17 is a graph illustrating the results of continuous ethanol production using the acid-treated saccharified solution in Example 6.

Namely, a continuous fermentation test was carried out at a concentration close to an undiluted solution (10:1) under the conditions of a flow rate of 16 mL/hour, D=0.25/hour and 30° C. As a result, there was less residual sugar, and ethanol was produced in the theoretical yield. The average ethanol concentration was 3.73%, the yield was 92.20%, and the rate of ethanol formation was 10.27 g/L·hour (FIG. 17*a*). Further, in order to study high speed continuous fermentation for producing ethanol, the continuous fermentation was carried out by maintaining the above sugar concentration of the acid-treated saccharified solution at a flow rate of 32 ml/hour and D=0.50/hour in a thermostat at 30° C. As a result, glucose and xylose were consumed, and only a trace amount of mannose remained. The average ethanol concentration was 3.83%, the yield was 86.56%, and the rate of ethanol formation was 20.88 g/L·hour (FIG. 17*b*). In view of this, ethanol was produced in a yield close to the theoretical yield, even if the dilution ratio was 0.50/hour.

INDUSTRIAL APPLICABILITY

As discussed above, according to the present invention, an energy-saving high-efficiency conversion process for bioethanol can be established by using a fermentative bacterial strain capable of fermenting glucose, mannose and xylose simultaneously which can produce ethanol by fermenting a saccharified solution of cellulose-type and lignocellulose-type biomass resources.

SEQUENCE LISTING FREE TEXT

SEQ ID NO: 1: Designed oligonucleotide primer to amplify DNA encoding *E. coli* manA;
SEQ ID NO: 2: Designed oligonucleotide primer to amplify DNA encoding *E. coli* manA;
SEQ ID NO: 3: Designed oligonucleotide primer to amplify DNA encoding *E. coli* manA;
SEQ ID NO: 4: Designed oligonucleotide primer to amplify DNA encoding *E. coli* manA;
SEQ ID NO: 5: Designed oligonucleotide primer to amplify DNA encoding *Zymomonas mobilis* genome E2 gene portion;
SEQ ID NO: 6: Designed oligonucleotide primer to amplify DNA encoding *Zymomonas mobilis* genome E2 gene portion;
SEQ ID NO: 7: Designed oligonucleotide primer to amplify DNA encoding *Zymomonas mobilis* genome E2 gene portion;
SEQ ID NO: 8: Designed oligonucleotide primer to amplify DNA encoding *Zymomonas mobilis* genome E2 gene portion;
SEQ ID NO: 9: Designed oligonucleotide primer to amplify DNA encoding *E. coli* xylA, B;
SEQ ID NO: 10: Designed oligonucleotide primer to amplify DNA encoding *E. coli* xylA, B;
SEQ ID NO: 11: Designed oligonucleotide primer to amplify DNA encoding *E. coli* xylA, B;
SEQ ID NO: 12: Designed oligonucleotide primer to amplify DNA encoding *E. coli* xylA, B;
SEQ ID NO: 13: Designed oligonucleotide primer to amplify DNA encoding *E. coli* tal;
SEQ ID NO: 14: Designed oligonucleotide primer to amplify DNA encoding *E. coli* tal;
SEQ ID NO: 15: Designed oligonucleotide primer to amplify DNA encoding *E. coli* tal;
SEQ ID NO: 16: Designed oligonucleotide primer to amplify DNA encoding *E. coli* tal;
SEQ ID NO: 17: Designed oligonucleotide primer to amplify DNA encoding *E. coli* tkt;
SEQ ID NO: 18: Designed oligonucleotide primer to amplify DNA encoding *E. coli* tkt.

The invention claimed is:

1. A fermentative recombinant *Zymomonas mobilis* bacterium capable of fermenting glucose, mannose and xylose simultaneously, which is *Zymomonas mobilis* ZM mx42 (FERM BP-11025), which is produced by:
   integrating a gene encoding a phosphomannose isomerase of *Escherichia coli* origin into a levansucrase gene located on the chromosome of *Zymomonas mobilis* ZMcs (FERM BP-11024) as a host by double cross-over according to a homologous recombination method, and
   introducing a recombinant DNA into said host which is formed by binding a DNA fragment containing genes encoding a xylose isomerase, a xylulokinase, a transaldolase and a transketolase, wherein said genes comprised in said vector are of *Escherichia coli* origin.

2. A process for producing ethanol comprising allowing a saccharified solution of cellulose-type or lignocellulose-type biomass resources and the fermentative bacterium capable of fermenting glucose, mannose and xylose simultaneously according to claim 1, which has been immobilized on an immobilized carrier, to contact with each other, thereby fermenting the saccharified solution to obtain a fermented solution, and recovering ethanol from the fermented solution.

3. The process for producing ethanol according to claim 2, wherein the biomass resource is a ligneous biomass resource.

4. The process for producing ethanol according to claim 2, wherein the saccharified solution is continuously fed into a reactor packed with the immobilized fermentative bacterium, thereby allowing the saccharified solution and the fermentative bacterium to contact with each other to obtain a fermented solution, collecting the fermented solution continuously, and recovering ethanol therefrom.

5. A process for producing ethanol comprising allowing a saccharified solution of cellulose-type and lignocellulose-type biomass resources and the fermentative bacterium capable of fermenting glucose, mannose and xylose simultaneously according to claim 1, which has been immobilized on an immobilized carrier, to contact with each other, thereby fermenting the saccharified solution to obtain a fermented solution, and recovering ethanol from the fermented solution.

6. The process for producing ethanol according to claim 5, wherein the biomass resource is a ligneous biomass resource.

* * * * *

SEQUENCE LISTING

<160> NUMBER OF SEQ ID NOS: 18

<210> SEQ ID NO 1
<211> LENGTH: 35
<212> TYPE: DNA
<213> ORGANISM: Artificial Sequence
<220> FEATURE:
<223> OTHER INFORMATION: Synthetic oligonucleotide primer to amplify
      DNA encoding E. coli manA

<400> SEQUENCE: 1
cggaattcgt tcgatcaaca acccgaatcc tatcg                               35

<210> SEQ ID NO 2
<211> LENGTH: 50
<212> TYPE: DNA
<213> ORGANISM: Artificial Sequence
<220> FEATURE:
<223> OTHER INFORMATION: Synthetic oligonucleotide primer to amplify
      DNA encoding E. coli manA

<400> SEQUENCE: 2
cttaataagt taggagaata aacatgcaaa aactcattaa ctcagtgcaa               50

<210> SEQ ID NO 3
<211> LENGTH: 50
<212> TYPE: DNA
<213> ORGANISM: Artificial Sequence
<220> FEATURE:
<223> OTHER INFORMATION: Synthetic oligonucleotide primer to amplify
      DNA encoding E. coli manA

<400> SEQUENCE: 3
ttgcactgag ttaatgagtt tttgcatgtt tattctccta acttattaag               50

<210> SEQ ID NO 4
<211> LENGTH: 35
<212> TYPE: DNA
<213> ORGANISM: Artificial Sequence
<220> FEATURE:
<223> OTHER INFORMATION: Synthetic oligonucleotide primer to amplify
      DNA encoding E. coli manA

<400> SEQUENCE: 4
cgcggatcct tacagcttgt tgtaaacacg cgcta                               35

<210> SEQ ID NO 5
<211> LENGTH: 50
<212> TYPE: DNA
<213> ORGANISM: Artificial Sequence
<220> FEATURE:
<223> OTHER INFORMATION: Synthetic oligonucleotide primer to amplify
      DNA encoding Zymomonas mobilis genome E2 gene portion

<400> SEQUENCE: 5
acttaataag ttaggagaat aaacatgttg aataaagcag gcattgcaga               50

<210> SEQ ID NO 6
<211> LENGTH: 35
<212> TYPE: DNA
<213> ORGANISM: Artificial Sequence
<220> FEATURE:
<223> OTHER INFORMATION: Synthetic oligonucleotide primer to amplify
      DNA encoding Zymomonas mobilis genome E2 gene portion

<400> SEQUENCE: 6

```
gctctagatc attatttatt caataaagac agggc                              35
```

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide primer to amplify
      DNA encoding Zymomonas mobilis genome E2 gene portion

<400> SEQUENCE: 7

```
agcaaataat ttctgggatt tccgc                                         25
```

<210> SEQ ID NO 8
<211> LENGTH: 16
<212> TYPE: DNA
<213> ORGANISM: Artificial Sequence
<220> FEATURE:
<223> OTHER INFORMATION: Synthetic oligonucleotide primer to amplify
      DNA encoding Zymomonas mobilis genome E2 gene portion

<400> SEQUENCE: 8

```
aggccgctcc gtctgg                                                   16
```

<210> SEQ ID NO 9
<211> LENGTH: 35
<212> TYPE: DNA
<213> ORGANISM: Artificial Sequence
<220> FEATURE:
<223> OTHER INFORMATION: Synthetic oligonucleotide primer to amplify
      DNA encoding E. coli xylA, B

<400> SEQUENCE: 9

```
cggaattcgt tcgatcaaca acccgaatcc tatcg                              35
```

<210> SEQ ID NO 10
<211> LENGTH: 51
<212> TYPE: DNA
<213> ORGANISM: Artificial Sequence
<220> FEATURE:
<223> OTHER INFORMATION: Synthetic oligonucleotide primer to amplify
      DNA encoding E. coli xylA, B

<400> SEQUENCE: 10

```
tactggaata aatggtcttc gttatgcaag cctattttga ccagcctcga t            51
```

<210> SEQ ID NO 11
<211> LENGTH: 49
<212> TYPE: DNA
<213> ORGANISM: Artificial Sequence
<220> FEATURE:
<223> OTHER INFORMATION: Synthetic oligonucleotide primer to amplify
      DNA encoding E. coli xylA, B

<400> SEQUENCE: 11

```
atcgactggt caaaataggc ttgcataacg aagaccattt attccagta               49
```

<210> SEQ ID NO 12
<211> LENGTH: 35
<212> TYPE: DNA
<213> ORGANISM: Artificial Sequence
<220> FEATURE:
<223> OTHER INFORMATION: Synthetic oligonucleotide primer to amplify
      DNA encoding E. coli xylA, B

<400> SEQUENCE: 12

```
cggaattcat gcatagttgc caaaagttgc tgtca                              35
```

<210> SEQ ID NO 13
<211> LENGTH: 40
<212> TYPE: DNA
<213> ORGANISM: Artificial Sequence
<220> FEATURE:
<223> OTHER INFORMATION: Synthetic oligonucleotide primer to amplify
      DNA encoding E. coli tal

<400> SEQUENCE: 13
cggaattctc gagctccagt tactcaatac gtaacaataa                           40

<210> SEQ ID NO 14
<211> LENGTH: 50
<212> TYPE: DNA
<213> ORGANISM: Artificial Sequence
<220> FEATURE:
<223> OTHER INFORMATION: Synthetic oligonucleotide primer to amplify
      DNA encoding E. coli tal

<400> SEQUENCE: 14 aagatttta gaaaggtttc gatatgacgg acaaattgac ctcccttcgt                 50

<210> SEQ ID NO 15
<211> LENGTH: 50
<212> TYPE: DNA
<213> ORGANISM: Artificial Sequence
<220> FEATURE:
<223> OTHER INFORMATION: Synthetic oligonucleotide primer to amplify
      DNA encoding E. coli tal

<400> SEQUENCE: 15
acgaagggag gtcaatttgt ccgtcatatc gaaacctttc ttaaaatctt                50

<210> SEQ ID NO 16
<211> LENGTH: 50
<212> TYPE: DNA
<213> ORGANISM: Artificial Sequence
<220> FEATURE:
<223> OTHER INFORMATION: Synthetic oligonucleotide primer to amplify
      DNA encoding E. coli tal

<400> SEQUENCE: 16
cattttgact accagatcta gattacagca gatcgccgat catttttcc                50

<210> SEQ ID NO 17
<211> LENGTH: 40
<212> TYPE: DNA
<213> ORGANISM: Artificial Sequence
<220> FEATURE:
<223> OTHER INFORMATION: Synthetic oligonucleotide primer to amplify
      DNA encoding E. coli tkt

<400> SEQUENCE: 17
cggaattctc gagctccagt tactcaatac gtaacaataa                           40

<210> SEQ ID NO 18
<211> LENGTH: 50
<212> TYPE: DNA
<213> ORGANISM: Artificial Sequence
<220> FEATURE:
<223> OTHER INFORMATION: Synthetic oligonucleotide primer to amplify
      DNA encoding E. coli tkt

<400> SEQUENCE: 18
cggcatgcct cgaggcaaac ggacattatc aaggtaataa aaaaggtcgc                50